United States Patent [19]
Fecteau et al.

[11] Patent Number: 5,825,455
[45] Date of Patent: Oct. 20, 1998

[54] ASPHERIC PLANO EYEWEAR

[75] Inventors: Keith Fecteau, Wilbraham, Mass.; James Hall, Lincoln, R.I.; Raoul Desy, Sturbridge; John Salce, Auburn, both of Mass.; David M. Hasenauer, Monrovia, Calif.

[73] Assignee: Cabot Safety Intermediate Corporation, Southbridge, Mass.

[21] Appl. No.: 806,832

[22] Filed: Feb. 26, 1997

Related U.S. Application Data

[63] Continuation-in-part of Ser. No. 641,901, May 2, 1996, abandoned.

[51] Int. Cl.$^6$ .............................. G02C 7/02; G02C 1/13
[52] U.S. Cl. ......................................... 351/159; 351/41
[58] Field of Search ............................... 351/159, 160 R, 351/160 H, 41, 43–44; 2/6.3, 425–426

[56] References Cited

U.S. PATENT DOCUMENTS

| D. 135,237 | 3/1943 | Bausch | D16/101 |
|---|---|---|---|
| D. 140,506 | 3/1945 | Joyce | D16/101 |
| D. 141,029 | 4/1945 | Splaine | D57/1 |

(List continued on next page.)

U.S. PATENT DOCUMENTS

| D. 141,193 | 5/1945 | Baratelli | D57/1 |
|---|---|---|---|
| D. 144,560 | 4/1946 | Hansen | D57/1 |
| D. 163,869 | 7/1951 | Hinman | D57/1 |
| D. 198,052 | 4/1964 | Petitto | D57/1 |
| D. 198,996 | 8/1964 | Lissac | D57/1 |
| D. 199,150 | 9/1964 | Carmichael | D57/1 |
| D. 199,932 | 12/1964 | Shindler | D57/1 |
| D. 199,933 | 12/1964 | Shindler | D57/1 |
| D. 201,393 | 6/1965 | Thomas | D57/1 |
| D. 202,129 | 8/1965 | Marchi | D57/1 |
| D. 203,136 | 12/1965 | Shindler | D57/1 |
| D. 204,957 | 5/1966 | Dym | D57/1 |
| D. 228,028 | 7/1973 | Leblanc et al. | D57/1 |
| D. 228,583 | 10/1973 | Leblanc | D2/234 |
| D. 231,260 | 4/1974 | Jelinek | D57/1 |
| D. 268,683 | 4/1983 | Tenny | D16/102 |
| D. 270,165 | 8/1983 | Burns | D16/119 |
| D. 323,333 | 1/1992 | Jannard et al. | D16/112 |
| D. 344,282 | 2/1994 | Hirschman | D16/102 |
| D. 358,828 | 5/1995 | Jannard et al. | D16/101 |
| D. 367,664 | 3/1996 | Simioni | D16/309 |
| 2,537,047 | 1/1951 | Gatten | 351/159 |
| 3,133,982 | 5/1964 | Janz | 351/62 |
| 3,140,390 | 7/1964 | Smith et al. | 607/109 |
| 3,218,765 | 11/1965 | Volk | 451/42 |
| 3,233,249 | 2/1966 | Baratelli et al. | 2/443 |
| 3,283,446 | 11/1966 | Feinbloom | 451/231 |

(List continued on next page.)

FOREIGN PATENT DOCUMENTS 485155  7/1952  Canada.

*Primary Examiner*—Georgia Epps
*Assistant Examiner*—Jordan M. Schwartz
*Attorney, Agent, or Firm*—Fishman, Dionne, Cantor & Colburn

[57] ABSTRACT

A novel plano lens and eyewear incorporating such lens is presented wherein the plano lens comprises a front surface curvature which is created by rotating an aspheric shape about an axis which is offset from an axis of the aspheric shape. In a preferred embodiment, the aspheric shape is an ellipse or at least is an aspheric shape, a segment of which has an elliptical arc. This elliptical arc is rotated about an axis spaced (offset) some distance from a major or minor axis of the ellipse. In a more preferred embodiment, the ellipse is rotated about an axis spaced from and parallel to the major or minor axis of the ellipse, but in the same plane as the ellipse. The resulting surface of this preferred lens configuration will have a cross-section in a first axis which is a segment of an ellipse, and a cross-section in a second axis (perpendicular to the first axis) which is a segment of a circle. A significant feature of the preferred front lens configuration is that the surface generated is rotationally symmetric.

62 Claims, 15 Drawing Sheets

U.S. PATENT DOCUMENTS

| | | | |
|---|---|---|---|
| 3,394,980 | 7/1968 | Dym | 351/41 |
| 3,419,909 | 1/1969 | Spain | 2/174 |
| 3,526,449 | 9/1970 | Bollé et al. | 351/41 |
| 3,605,116 | 9/1971 | Simpson et al. | 2/445 |
| 3,623,800 | 11/1971 | Volk | 351/169 |
| 3,722,986 | 3/1973 | Tagnon | 351/176 |
| 3,950,082 | 4/1976 | Volk | 351/169 |
| 4,002,439 | 1/1977 | Volk | 451/42 |
| 4,240,718 | 12/1980 | Wichers | 351/62 |
| 4,264,987 | 5/1981 | Runckel | 2/428 |
| 4,630,906 | 12/1986 | Bammert et al. | 351/159 |
| 4,670,915 | 6/1987 | Evans | 2/450 |
| 4,674,136 | 6/1987 | Ladewig | 2/428 |
| 4,674,851 | 6/1987 | Jannard | 351/47 |
| 4,741,611 | 5/1988 | Burns | 351/44 |
| 4,776,045 | 10/1988 | Mysliwiec et al. | 2/426 |
| 4,786,125 | 11/1988 | Magarinos et al. | 359/7 |
| 4,810,080 | 3/1989 | Grendol et al. | 351/41 |
| 4,824,233 | 4/1989 | Jannard | 351/47 |
| 4,843,655 | 7/1989 | Hegendörfer | 2/449 |
| 4,859,048 | 8/1989 | Jannard | 351/159 |
| 4,867,550 | 9/1989 | Jannard | 351/47 |
| 4,934,807 | 6/1990 | Bolle et al. | 351/62 |
| 4,955,087 | 9/1990 | Perez et al. | 2/12 |
| 4,976,530 | 12/1990 | Mackay et al. | 351/44 |
| 4,978,182 | 12/1990 | Tedesco | 359/15 |
| 5,032,017 | 7/1991 | Bollé et al. | 351/116 |
| 5,050,981 | 9/1991 | Roffman | 351/177 |
| 5,204,700 | 4/1993 | Sansalone | 351/43 |
| 5,208,614 | 5/1993 | Jannard | 351/41 |
| 5,235,357 | 8/1993 | Winthrop et al. | 351/159 |
| 5,339,119 | 8/1994 | Gardner | 351/158 |
| 5,357,292 | 10/1994 | Wiedner | 351/105 |
| 5,371,555 | 12/1994 | Nagel | 351/57 |
| 5,379,463 | 1/1995 | Schleger et al. | 2/431 |
| 5,381,192 | 1/1995 | Canavan et al. | 351/118 |
| 5,387,949 | 2/1995 | Tackles | 351/121 |
| 5,426,473 | 6/1995 | Riehm | 351/121 |
| 5,438,710 | 8/1995 | McDonald et al. | 2/439 |
| 5,457,505 | 10/1995 | Canavan et al. | 351/120 |
| 5,495,303 | 2/1996 | Kolentsi | 351/43 |
| 5,604,547 | 2/1997 | Davis et al. | 351/44 |
| 5,648,832 | 7/1997 | Houston et al. | 351/159 |

R1 ≠ R2

R1 ≠ R2

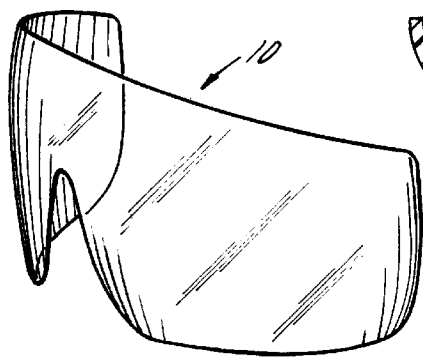
FIG. 11
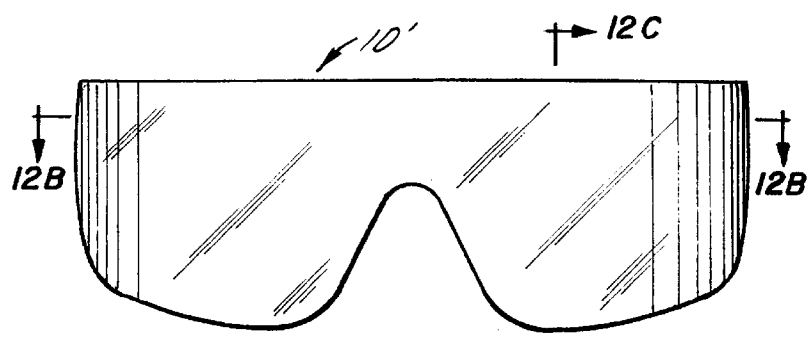
FIG. 12B
FIG. 12A
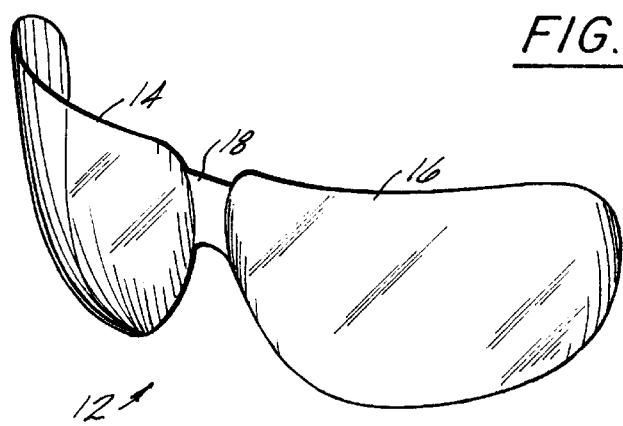
FIG. 13
FIG. 12C
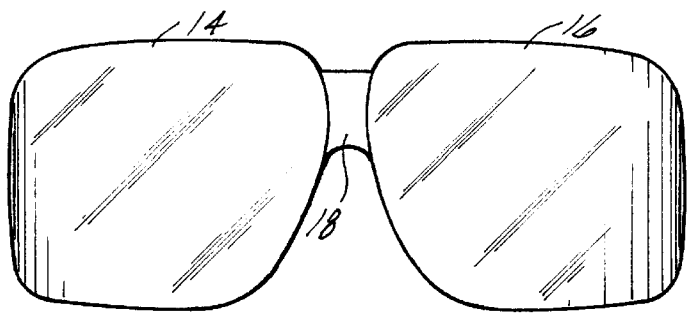
FIG. 14
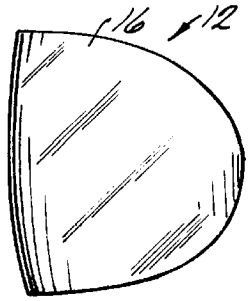
FIG. 15

ASPHERIC PLANO EYEWEAR

CROSS-REFERENCE TO RELATED APPLICATIONS

This is a continuation-in-part of application Ser. No. 08/641,901 filed May 2, 1996 now abandoned.

FIELD OF THE INVENTION

This invention relates generally to eyewear. More particularly, this invention relates to plano eyewear for use in safety and recreational (i.e., sports) applications. Examples of suitable eyewear applications include spectacles, goggles, faceshields, respirator lenses, visors, helmets and the like.

BACKGROUND OF THE INVENTION

Traditional plano (that is, non corrective or zero power) eyewear is constructed using lenses which are flat or spherical. A spherical lens surface is obtained when a circle is rotated about its diameter. Prior art FIGS. 1 and 2 depict a conventional spherical lens where FIG. 1 is a unitary spherical lens and FIG. 2 is a bispheric lens. As shown in FIGS. 1 and 2, the lens surface is a segment of a sphere such that a cross-section taken in any meridian through the center of the sphere will reveal an arc of constant radius R.

More recently, in an effort to improve protection to the wearer's eyes, attempts have been made to allow the lenses to curve along more of the wearer's face, that is, to achieve a larger wrap depth so as to protect the sides of the eyes. This has been accomplished using toric and cylindrical surfaces, all of which have been based on circular or spherical geometries. A circular toric surface is obtained when a circle is rotated about an axis which is located in the same plane as the circle, but at some distance from the diameter of the circle. The resulting three dimensional shape is a donut or toroid and the toric lens consists of a section of that formed donut. Prior art FIGS. 3 and 4 depict toric lenses where FIG. 3 is a unitary circular toric lens and FIG. 4 is a bi-toric lens. In both FIGS. 3 and 4, the resulting lens has a constant radius of curvature in the horizontal meridian of $R_2$ and a constant radius of curvature in the vertical meridian of $R_1$. Prior art examples of toric plano eyewear is disclosed in U.S. Pat. Nos. 4,867,550 to Jannard and 4,741,611 to Burns.

A cylinder is obtained when a circle is rotated about an axis which is located an infinite distance from the diameter of the circle. Prior art FIG. 5 depicts a unitary cylindrical lens used in eyewear. The cylinder can also be described as the surface obtained when a circle is extruded in a direction perpendicular to the plane of the circle. As shown in FIG. 5, the resulting lens has a constant radius of curvature $R_1$ in the horizontal meridian and a vertical axis radius of curvature $R_2$ equal to $\infty$ (which is essentially a straight line). Prior art examples of cylindrical plano eyewear are disclosed in U.S. Pat. Nos. 4,674,851 and 4,859,048 to Jannard.

As mentioned, all four of the aforementioned lens surfaces (flat, spherical, toric and cylindrical) are based on circular or spherical geometries. Several favorable advantages resulting from the use of such geometries are that the optical performance is easily predictable and the lens surfaces lend themselves easily to manufacture including mold production and lap polishing.

However, the foregoing conventional lens surfaces also suffer from certain serious drawbacks and deficiencies. For example, when spherical, toric or cylindrical lenses are used in plano safety eyewear, it is almost always necessary to have a separate sideshield for lateral protection of the eye. In some commercial designs, the sideshield is a separate component which is attached to, or integrally part of, the temple. In other commercial designs, the sideshield is integrally molded or formed into the lens. In the latter case there is an obvious, visible line of demarcation between the lens, and what is considered to be the sideshield. An example in the prior art of the requirements for such sideshields (either as a separate component or as an integrally molded feature) is described in U.S. Pat. No. 5,381,192 and shown in FIG. 6.

Although lenses based on circular and spherical geometries are easier to produce and their optical properties, easier to predict, design flexibility is limited because the radii in the horizontal and vertical axes are constant. Attempts have been made to design unitary lenses having integrally molded sideshields and no visible line of demarcation between the lens and the sideshield area. However, such lenses (which are made with spherical, cylindrical or circular toric surfaces) will not have sufficient wrap around the sides of the eyes to meet safety standards for lateral protection without being cosmetically and/or functionally unappealing. In order to achieve sufficient wrap, the spectacles have a tendency to take on a "bug-eyed" appearance. The "bug-eyed" appearance can be minimized by utilizing flatter curves, but a flatter curve does not wrap sufficiently close to the temple area. The "bug-eyed" appearance can be somewhat minimized by producing a circular toric. A circular toric lens can be flatter in the vertical meridian but still remains steep in the horizontal meridian. In order to achieve zero power, and to have lens edge thicknesses which will meet safety product impact requirements, and to have sufficient wrap without a separate sideshield, the lens center thickness tends to be relatively high, making the lens heavy and therefore less desirable. An examples of a prior art lens of this type is U.S. Pat. No. 5,032,017 to Bolle et al.

Still another lens surface which provides sufficient wrap but nevertheless maintains an unacceptably large "bug-eyed" appearance for many applications is disclosed in U.S. Pat. No. 4,978,182 to Tedesco. In this latter patent, an ellipse is rotated about its major axis to form an ellipsoid. A section of this ellipsoid is then used to form an eye shield. However, the resultant ellipsoidal lens surface protrudes substantially from the wearer's face and therefore suffers from the same "bug-eyed" appearance as does conventional spherical lens surfaces.

SUMMARY OF THE INVENTION

The above-discussed and other problems and deficiencies of the prior art are overcome or alleviated by the novel plano lens and eyewear incorporating such lens of the present invention. In accordance with the present invention, a plano lens comprises a front surface curvature which is created by rotating an aspheric shape about an axis which is offset from an axis of the aspheric shape. In a preferred embodiment, the shape is an ellipse or at least is an aspheric shape having an elliptical arc. This elliptical arc is rotated about an axis spaced (offset) some distance from a major or minor axis of the ellipse. In a more preferred embodiment, the ellipse is rotated about an axis spaced from and parallel to the major or minor axis of the ellipse. In a more preferred embodiment, the axis of rotation is coplanar with the ellipse. The resulting surface of this preferred lens configuration will have a cross-section in a first axis which is a segment of an ellipse, and a cross-section in a second axis (perpendicular to the first axis) which is a segment of a circle. A significant feature of the preferred front lens configuration is that the surface generated is rotationally symmetric.

It is preferable to orient the ellipse in the horizontal axis relative to the eye. The changing radius of curvature from relatively flat to progressively steeper in the horizontal meridian allows the lens to sufficiently wrap around the temple area. One large ellipse can be used to produce continuous lens wrapping around both temples, or separate ellipses can be used, one for each eye connected by a center bar, to make a one piece dual lens for a spectacle whereby each lens provides wrap for one of the wearer's temples.

While the front or outer lens surface will have the aspheric configuration described above, the back or inner lens surface will have a different shape which, together with the front lens surface, will result in a plano, substantially plano or zero power optical design. It will be appreciated that by "zero power" or piano, it is meant that the optics provide no substantial visually discernable correction to the human eye. As is well known to those in the art, spectacles are often designated as "zero power" despite providing some small, visually non-discernable correction such as, for example +0.125 to −0.250.

The novel aspheric plano lens configuration of the present invention provides many features and advantages, particularly when compared to prior art flat, spherical, cylindrical and circular toric plano lenses. First, the lens of this invention will have a high degree of wrap which will obviate the need for separate or integrally formed side shields. Indeed, the wrap is so extensive that the eyewear of this invention will meet the current safety standards of major geographical markets and market segments, again without the need for sideshields. In addition, the lens of this invention will have less of a "bug-eyed" appearance than known spherical or circular toric lens configurations while maintaining substantial wrap. Still another important feature of this invention is that the novel aspheric plano lens will have a lower center thickness than comparable conventional spherical, toric or cylindrical plano lenses and as a result, the eyewear of this invention will be substantially more lightweight.

The novel plano lens and associated eyewear is thus cosmetically pleasing, low weight, provides a high degree of lateral protection due to its high wrap, requires no sideshields, permits a thinner lens, exhibits no "bug-eyed" appearance and provides excellent protection for safety and recreational use. As a result of the foregoing, the plano lens of this invention finds excellent utility as protective lenses in the safety, recreation, or sports eyewear fields.

The above-discussed and other features and advantages of the present invention will be appreciated and understood by those skilled in the art from the following detailed description and drawings.

BRIEF DESCRIPTION OF THE DRAWINGS

Referring now to the FIGURES, wherein like elements are numbered alike in the several FIGURES:

FIG. 11 is a perspective view of a single piece continuous lens for spectacles in accordance with the present invention;

FIGS. 12A–C are respective front elevation and cross-section views of an alternative lens embodiment in accordance with the present invention;

FIGS. 13–15 are respective perspective, front elevation and side elevation views of a dual lens for spectacles in accordance with the present invention;

DESCRIPTION OF THE PREFERRED EMBODIMENT

In accordance with the present invention, an aspheric piano lens is provided preferably for use in conjunction with eyewear for the safety and recreational fields. The front surface of the aspheric piano lens of the present invention is created by rotating an aspheric shape (such as an ellipse) about an axis which is offset from and preferably coplanar with an axis of the aspheric shape. Thus, the surface generated is rotationally symmetrical and is aspheric. A section of the three dimensional shape formed by this symmetric rotation is then utilized as a piano lens.

Figure 1:
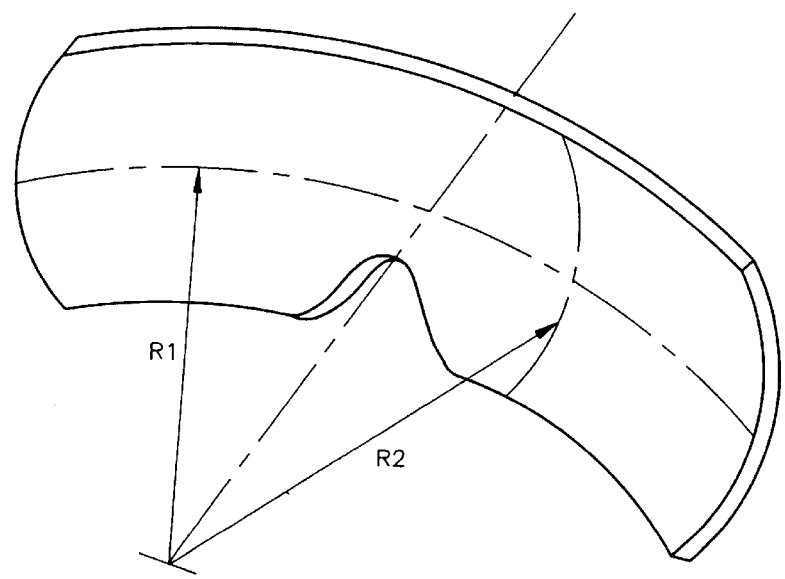
FIGS. 1 and 2 are perspective views of unitary spherical and bi-spheric lenses, respectively, in accordance with the prior art.
Figure 2:
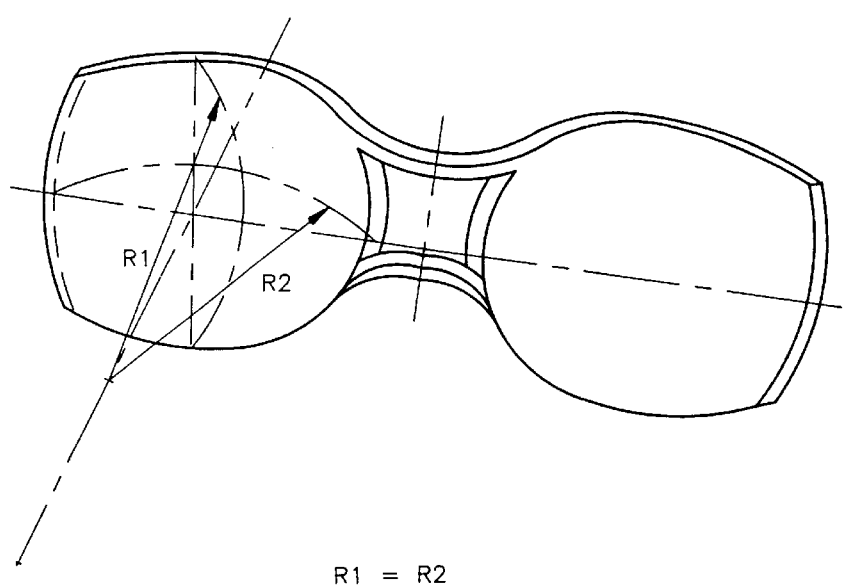
Figure 3:
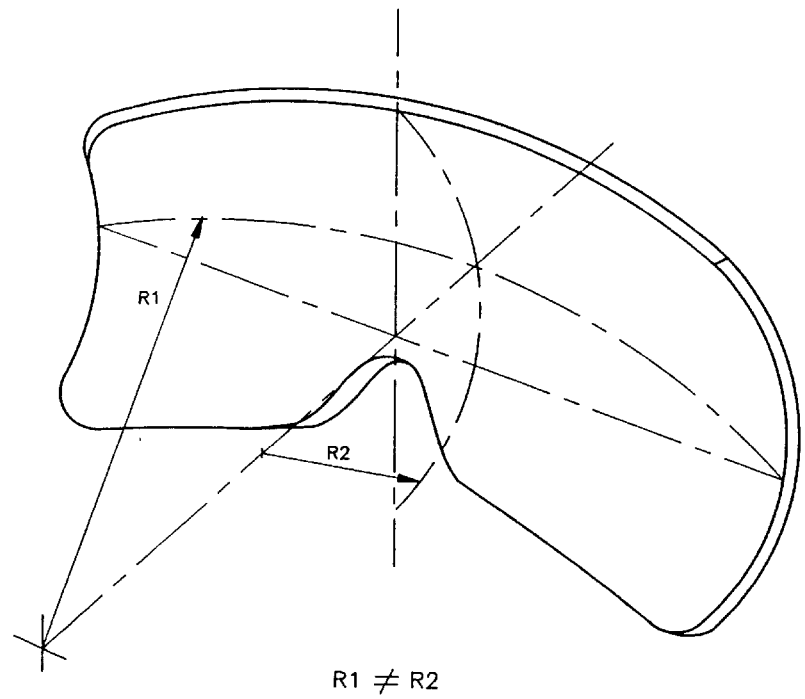
FIGS. 3 and 4 are perspective views of unitary circular toric and bi-toric lenses, respectively, in accordance with the prior art.
Figure 4:
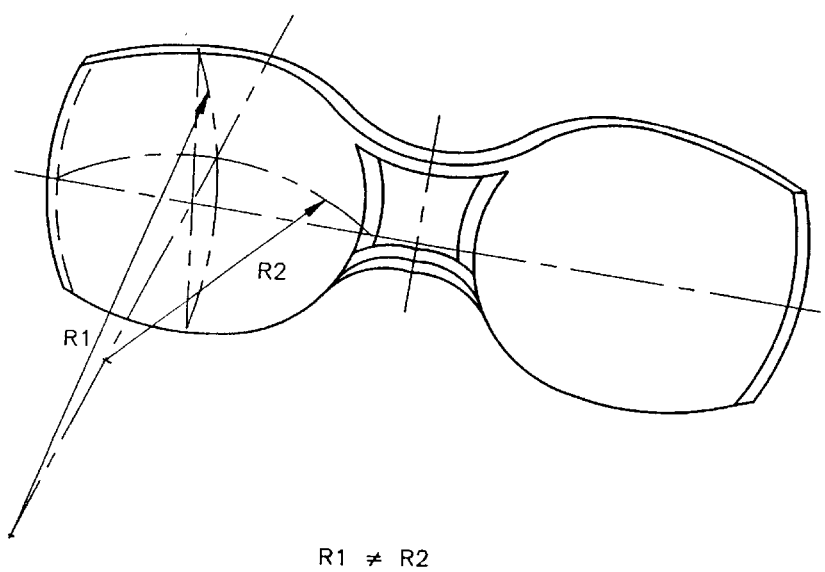
Figure 5:
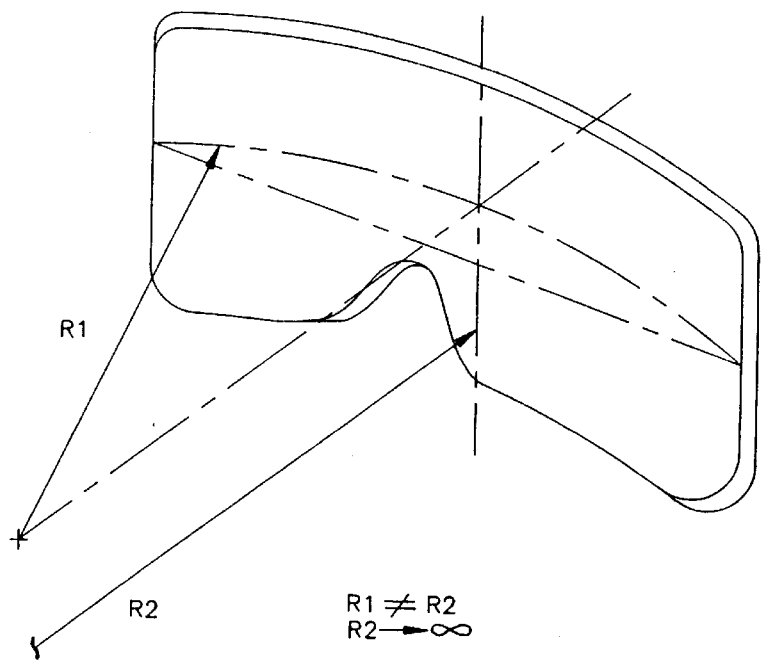
FIG. 5 is a perspective view of a unitary cylindrical lens in accordance with the prior art.
Figure 6:
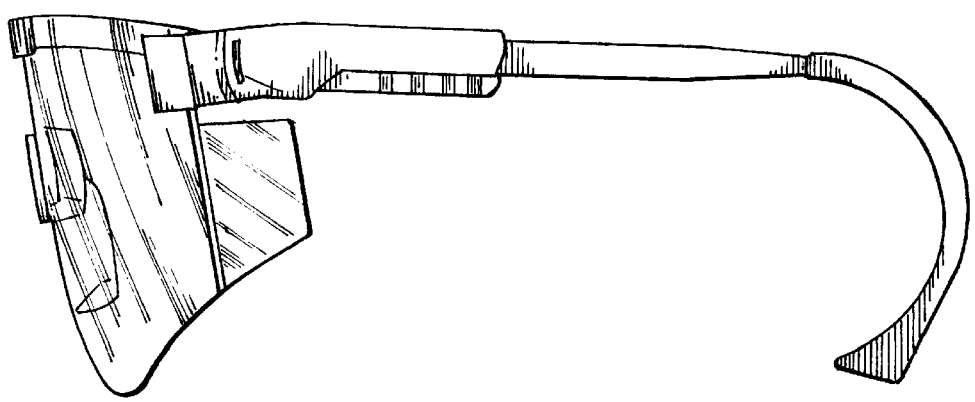
FIG. 6 is a side elevation view of a prior art protective spectacle with integrally molded sideshields.
Figure 7:
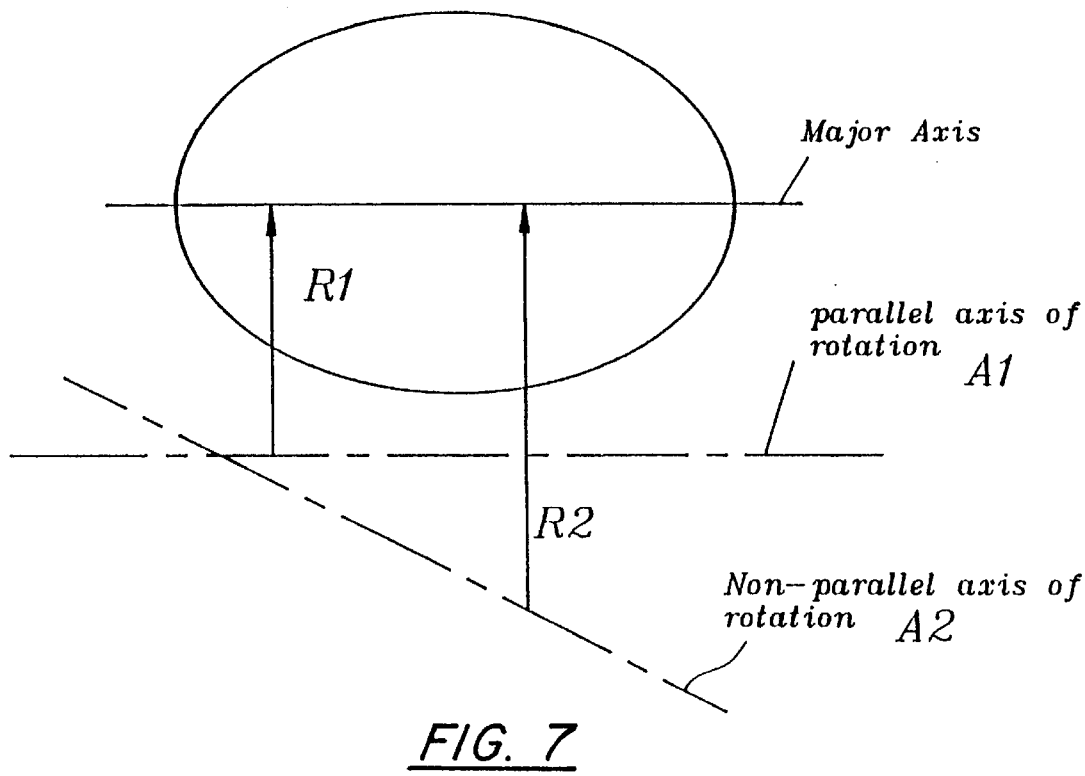
FIGS. 7 and 8 are diagrammatic views depicting the geometry used in forming the lenses surfaces in accordance with the present invention.
Figure 8:
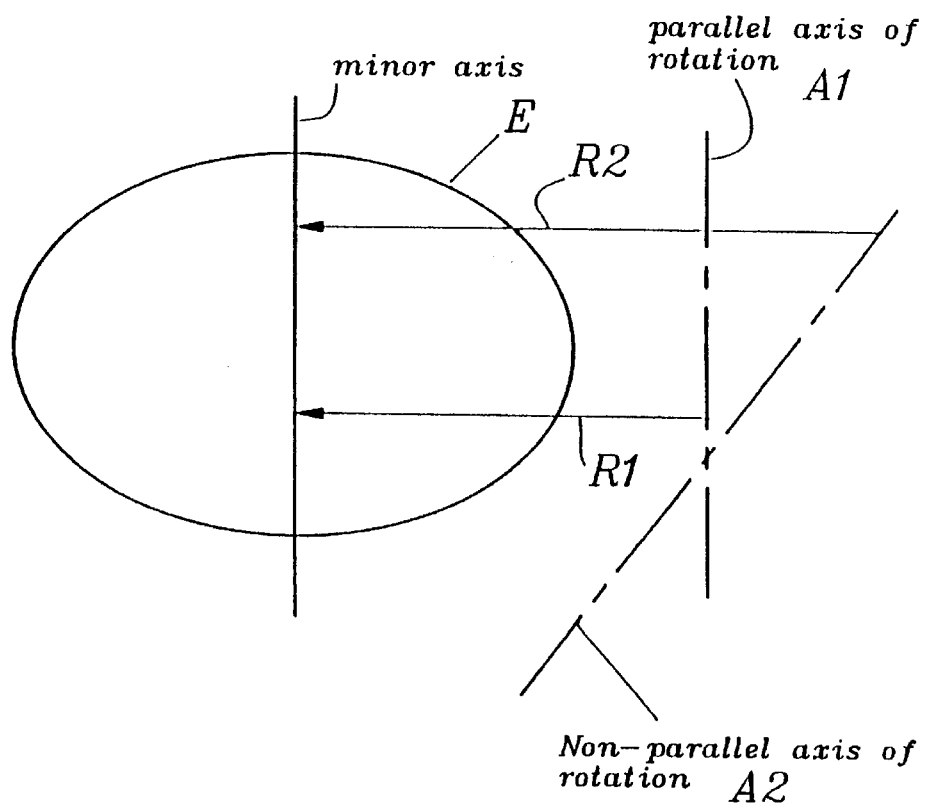

Preferably, the aspheric shape is an ellipse. Referring to FIGS. 7 and 8, diagrammatic FIGURES are shown of the manner in which the preferred lens configuration of the present invention is formed. Referring to FIG. 7, the front surface of the aspheric plano lens of this invention can be formed by rotating an ellipse E about an axis which is coplanar and offset from the major axis of the ellipse. The axis of rotation may be a parallel axis of rotation or a non parallel axis of rotation as shown in FIG. 7. Thus, for example, in one embodiment of this invention, the front lens surface may be formed from a section of the three dimensional shape formed by rotating ellipse E about the parallel axis of rotation $A_1$ which is spaced from the major axis of ellipse E by the distance $R_1$ but is parallel to the major axis and coplanar with the major axis. In an alternative embodiment, the lens of this invention is formed by a section of the three-dimensional shape defined by rotating ellipse E with respect to the axis $A_2$ which is not parallel to the major axis but is spaced from the major axis by the distance $R_2$ and is coplanar therewith.

FIG. 8 depicts two additional alternative embodiments of this invention wherein the front surface of the plano lens is formed from a section of the three dimensional shape defined by rotating the ellipse E by either the axis of rotation $A_1$ which is offset but parallel to the minor axis of ellipse E by the distance $R_1$ or the axis of rotation $A_2$ which is spaced from and is not parallel to the minor axis of ellipse E.

Figure 9:
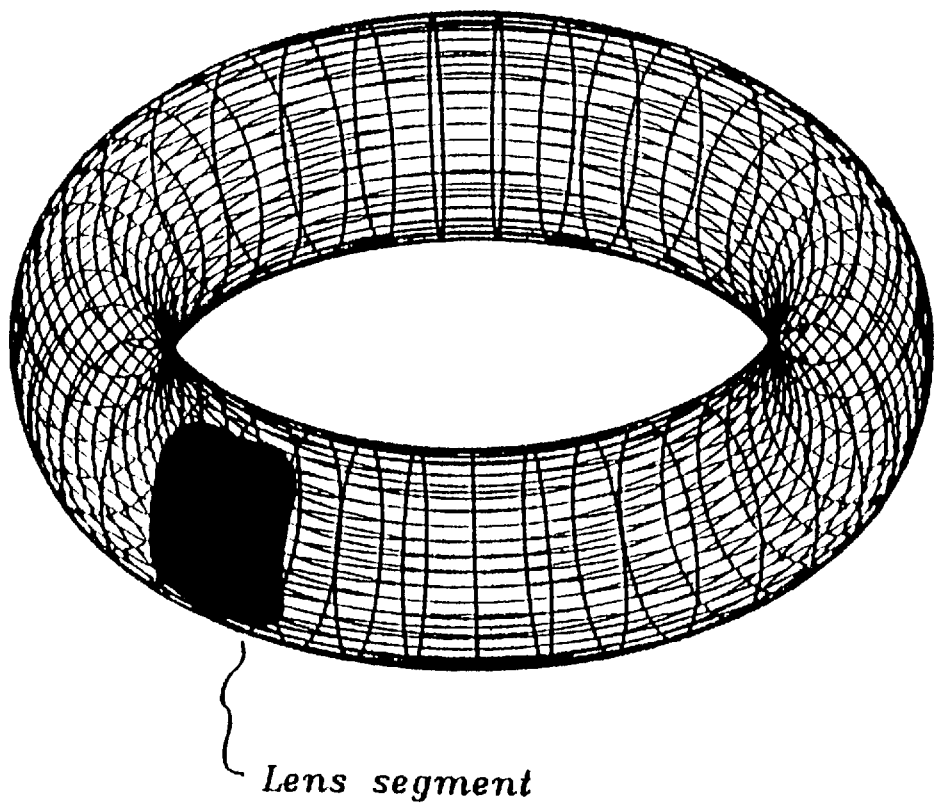
FIG. 9 is a perspective view of the three dimensional shape used to define the aspheric plano lenses of the present invention.

In all cases of FIGS. 7-8, the axis of rotation $A_1$, $A_2$ which is offset from either the major or minor axes is coplanar with the major or minor axes and the resulting three dimensional surface will have a cross-section in one axis which is a segment of an ellipse and a cross-section perpendicular to that axis which is a segment of a circle. As an example, FIG. 9 depicts the three dimensional shape formed by rotating ellipse E about the axis of rotation $A_1$ in FIG. 7. The front surface of a plano lens in accordance with the present invention can then be formed by selecting any appropriate segment from the three dimensional shape in FIG. 9 such as the lens segment indicated in the drawings.

In addition to the aforementioned embodiments, in still another embodiment of this invention, the "distance" from which the axis of rotation is offset from an axis of the aspheric (elliptical) shape may be an infinite distance in which case the resultant lens would have an elliptical cross-section in the horizontal axis and a straight line in the vertical axis. This alternative lens configuration is shown at 10' in FIGS. 12A-C.

The inner or back surface of the lens is also preferably an aspheric shape, however typically this back surface will be a shape that differs from the front surface. The shape of the back or interior lens surface is dictated by that shape which provides zero power or plano optics to the entire lens or at least to the viewing portion of the lens, it being understood that the lateral or side portions of the lens which wrap about the wearer's face do not necessarily require zero power optics.

Figure 10:
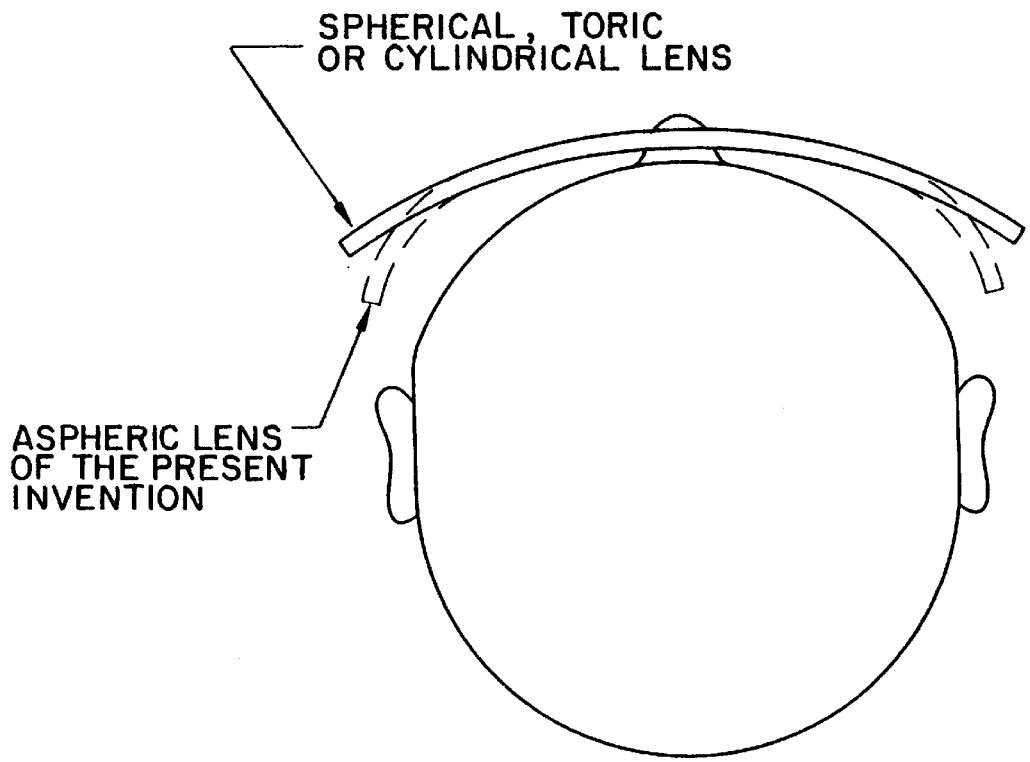
FIG. 10 is a diagrammatic top plan view comparing the aspheric piano lens of this invention to the prior art spherical, toric and cylindrical lenses.

Referring to FIG. 10, it is preferable to orient the ellipse in the horizontal axis relative to the eye. The changing radius of curvature from relatively flat to progressively steeper in the horizontal meridian allows the aspheric plano lens of this invention to sufficiently wrap around the temple area as schematically shown in FIG. 10. It will be appreciated that the novel aspheric lens configuration of the present invention provides significantly greater wrap than does the spherical, toric or cylindrical lenses found in the prior art and indicated diagrammatically in FIG. 10.

In accordance with this invention, one large ellipse can be used to produce a continuous lens wrapping around both temples such as shown at 10, 10' in FIGS. 11 and 12 or separate ellipses can be used, one for each eye, to make a dual lens for a spectacle whereby each lens provides wrap for one of the wearer's temples. A lens of this type is shown at 12 in FIGS. 13-15. While the separate lens portions 14 and 16 of lens 12 may be separated (and for example, interconnected by a simple frame), preferably lens portions 14 and 16 are integrally interconnected or molded by a center bar 18 to make one piece dual lenses for a spectacle.

The lenses of this invention are preferably molded, cast or formed from a suitable optically clear material such as polycarbonate, allyl diglycol carbonate (CR-39) or glass.

EXAMPLES OF LENS DESIGN

Example 1

Figure 16A:
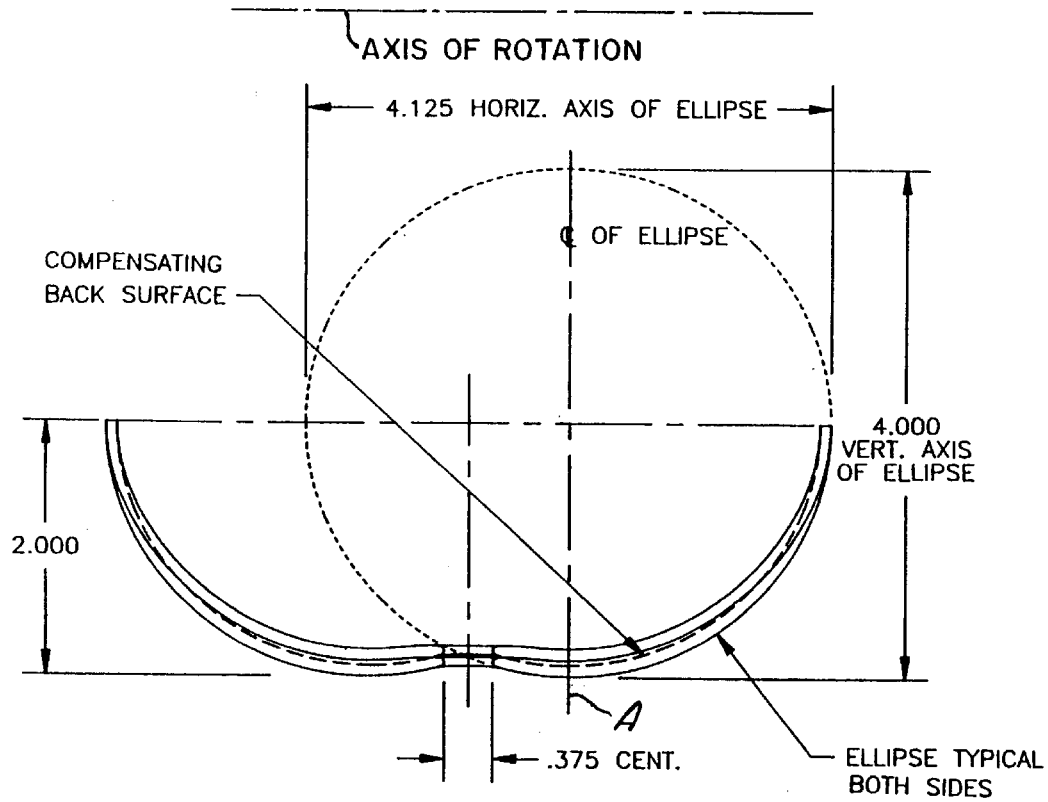
FIGS. 16A–C are respective top plan, front and side views of an actual example of a lens of the type shown in FIGS. 13–15 with critical dimensions and radii.
Figure 16B:
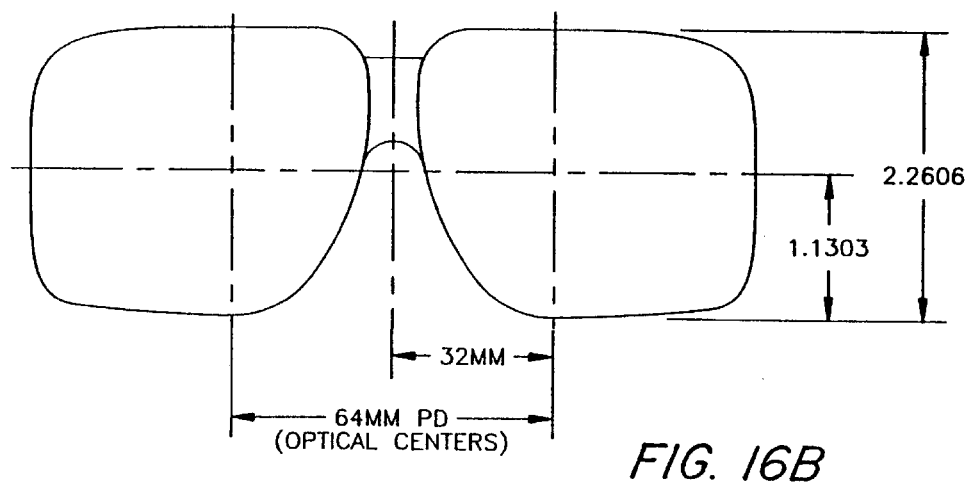
Figure 16C:
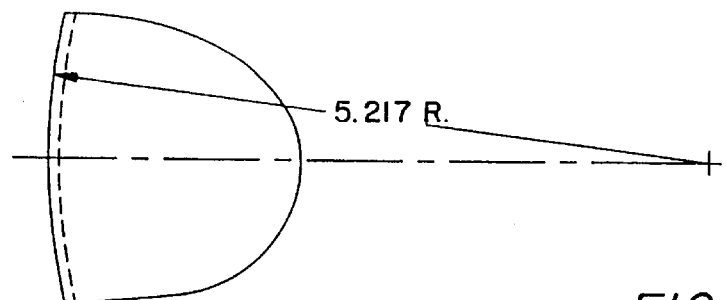

FIGS. 16A-C show an example of a spectacle of the type depicted in FIGS. 13-15 having two lenses; each with an elliptical cross section in the horizontal meridian. The major axis of the ellipse is 4.125" in length and the minor axis, 4.000". The vertical axis curvature of the lens is generated by rotating each of the ellipses about an axis located behind the spectacle a distance of 5.217" from the front vertex of the minor axis (point A). Any horizontal lens cross section taken through the axis of rotation will reveal an arcuate segment of the same ellipse. The back surface curvature is designed to provide zero power for straight ahead gaze at a pupillary distance of 64 mm. The two lenses are joined at the center by a connecting bar which can be integrally molded into the part.

Example 2

The same principle is applied to designing a unitary lens of the type depicted in FIGS. 11-12 which is generated by rotating a single ellipse, having a major axis length of about 5.700" and a minor axis length of about 4.000", about an axis located a distance of 5.217" from the front vertex of the minor axis. The back surface is designed to provide zero power for straight ahead gaze at a pupillary distance of 64 mm.

Example 3

Figure 17:
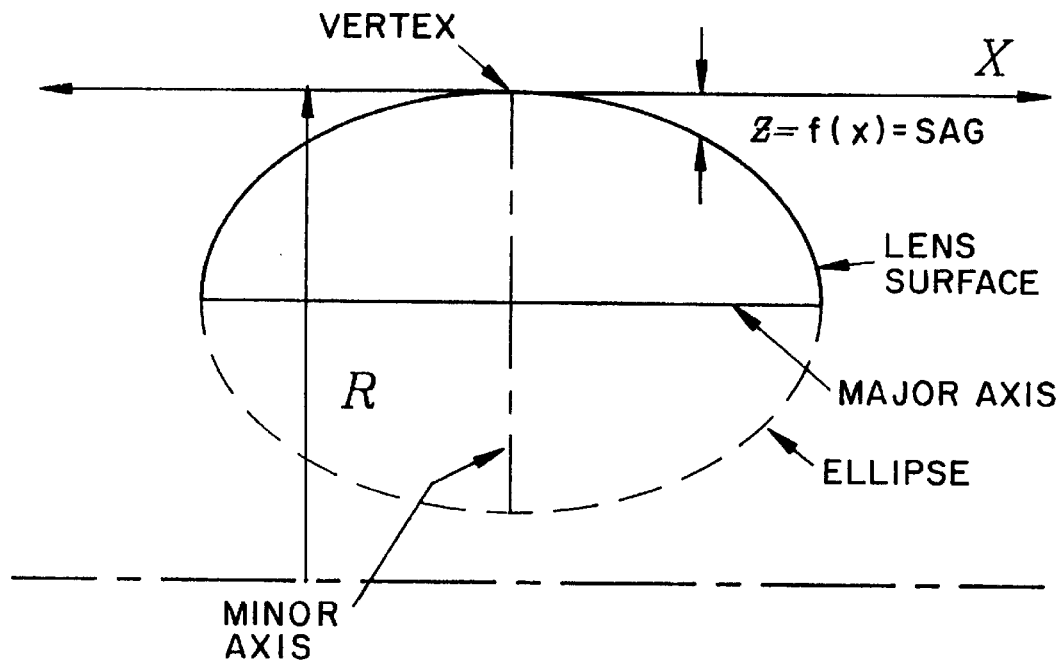
FIGS. 17 and 18 are diagrammatic views depicting lens design considerations in accordance with the present invention.

This example provides a more detailed analysis of the lens design in accordance with this invention. To start, as described earlier, the front surface of the lens is aspheric. The rear surface of the lens is designed to produce zero power at the design optical center. A cross-section along the horizontal meridian of the front surface of the aspheric lens reveals an arc having a non-constant radius of curvature (i.e., not a segment of a circle). The arc revealed by the preferred lens will be a segment of an ellipse (FIG. 17). Let x=the horizontal distance from the surface vertex along a tangent to the vertex of the arc. Let z=the sag of the curve, which is the perpendicular distance to a point on the arc from any point along the tangent to the vertex of the arc. Let the point (x,y)=0,0 be the vertex of the elliptical arc, which is the point on the ellipse through which the minor axis intersects (see FIG. 18). The sag of the horizontal cross-section of a rotationally symmetric asphere is given by:

$$z = \frac{cx^2}{1 + \{1 - ((1+k)c^2)x^2\}^{1/2}} + Ax^4 + Bx^6 + Cx^8 + Dx^{10} + \ldots \quad \text{(Eq. 1)}$$

where
- c=curvature
- k=conic constant
- z=conic sag
- x=horizontal distance from the surface vertex (x,z)=(0,0)
- A,B,C,D, etc.=high order aspheric constants=0 for an ellipse After an in depth analysis of the desired headspace, eyelash clearance, cosmetic appearance and lateral protection requirements, it was determined that the preferred spectacle should consist of two lenses, each having a horizontal cross-section which is a segment of an ellipse. The preferred ellipses each have a major axis of 4.125 inches in length and a minor axis of 4.000 inches in length. Although the optics are optimized for a pupillary distance of 2.520 in., the vertices of the ellipses will be spaced 1.473 inches from one another.

For either of the ellipses described above, $$c = .470 \text{ in}^{-1}$$
$$k = .0635$$

$$z = \frac{(.470)x^2}{1 + \{1 - ((1+.0635)(.470)^2)x^2\}^{1/2}} = \text{front surface horiz. sag}$$

Rotation of the arc about an axis located R=5.217 in. from the vertex and parallel to the major axis of the ellipse generates the front surface of the preferred lens (FIG. 17).

Figure 18:
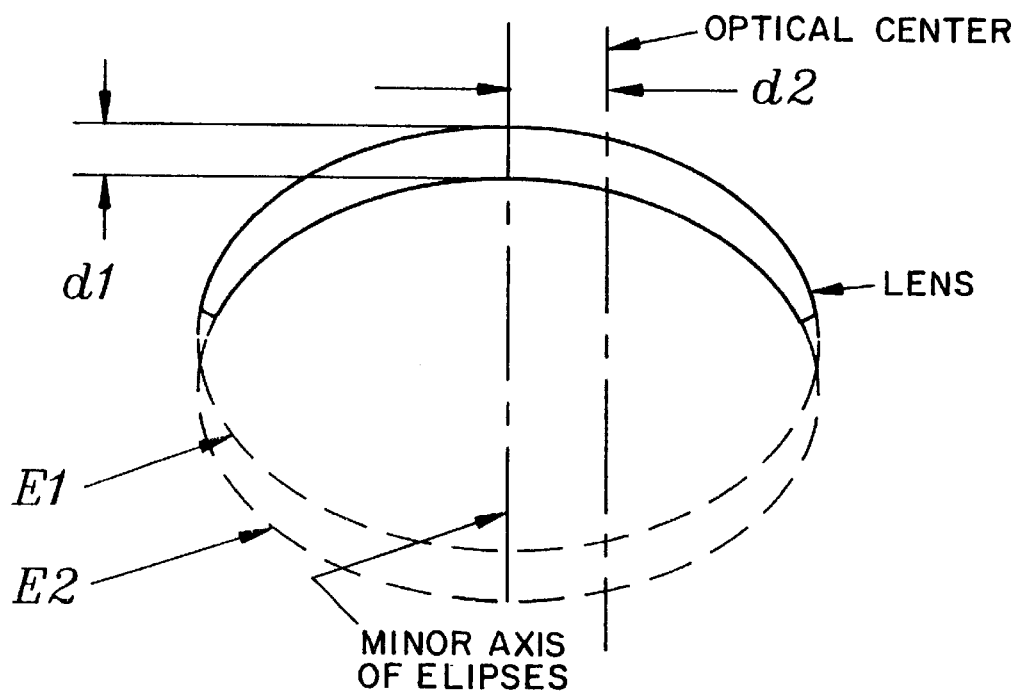

As mentioned above, spacing the vertices, or the minor axes, of the ellipses a distance of 1.473 in. from each other, creates the preferred dual lens spectacle. The rear surface of the lens is designed to provide substantially zero power at the design optical center, which is located at the point where x=0.473 in.=$d_2$ (FIG. 18).

The preferred rear surface is displaced a distance $d_1$ (FIG. 18) of 0.091 in. from the front surface at the surface vertex. To provide substantially zero power at the design optical center in the horizontal meridian, the sag of the preferred rear surface arc is defined from that point horizontally using following curvature and conic constants:

c=0.477 in$^{-1}$
k=0.094

Substituting into equation 1 for c, k and the variable x, in inches:

$$z = \frac{(.477)x^2}{1 + \{1 - ((1+.0974)(.477)^2)x^2\}^{1/2}} = \text{front surface horiz. sag}$$

In order for the power in the vertical axis to be substantially zero, the rear surface arc is preferably rotated about an axis located a distance r=5.184 in. from the vertex of the rear surface arc segment and parallel to the major axis of the ellipse of which the arc is a segment.

Additionally, if higher order aspheric terms are included in equation 1, it is possible to thin the center of the lens without allowing the edges to become too thin to resist impact. The resulting lens is light in weight, durable and has good optical performance characteristics.

One example of a rear surface which is not elliptical in the horizontal meridian is generated by applying the above curvature and conic constants, with the addition of a higher order aspheric term, G, such that:

c=0.477 in$^{-1}$
k=0.974
and
G=−1.77×10$^{-6}$ in$^{-15}$

Substituting:

$$z = \frac{(.477)x^2}{1 + \{1 - ((1+.0974)(.477)^2)x^2\}^{1/2}} +$$

$$(-1.77 \times 10^{-6})x^{16} = \text{rear surface horiz. sag}$$

In another example, $$c = .477 \text{ in}^{-1}$$
$$k = .0974$$
$$G = 1.28 \times 10^{-5} \text{ in}^{-15}$$
and
$$H = -2.88 \times 10^{-6} \text{ in}^{-17}$$

$$z = \frac{(.477)x^2}{1 + \{1 - ((1+.0974)(.477)^2)x^2\}^{1/2}} +$$

$$(1.28 \times 10^{-5})x^{16} + (-2.88 \times 10^{-6})x^{18} = \text{rear surface horiz. sag}$$

In the last two examples, the rear surface elliptical cross-section is displaced 0.91" from the front surface at the surface vertex. Both elliptical arcs are rotated about an axis located 5.184" from the surface vertex, parallel to the major axis of, and in the same plane as the ellipse, to generate the alternative rear surfaces.

Thus, as clearly shown in FIG. 18, and as is clear to a person of ordinary skill in the art from the several sag equations set forth above, in order to obtain substantially zero power in the lens of this invention, the lens thickness (that is, the distance "d" between the front and rear surfaces) must differ substantially throughout the lens. Thus, the thickness of a lens made in accordance with this invention will necessarily be of non-uniform thickness, that is the lens thickness will vary so as to provide zero power.

The aforementioned plano lens in accordance with this invention is useful for many applications in addition to use as safety spectacles. Such other uses include visors, goggles, masks, helmets and the like.

Figure 19:
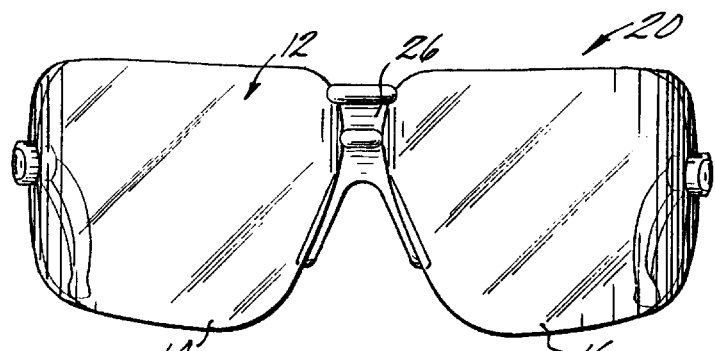
Figure 21:
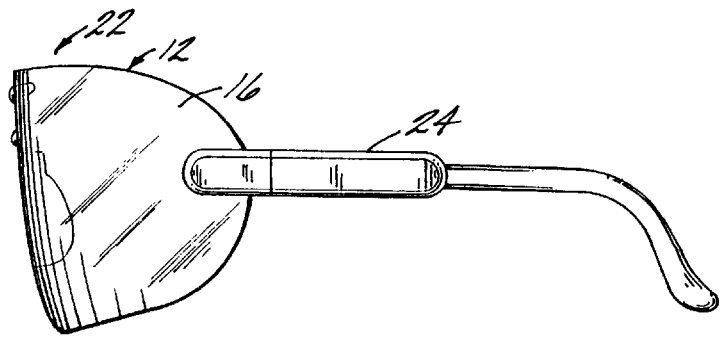
Figure 22:
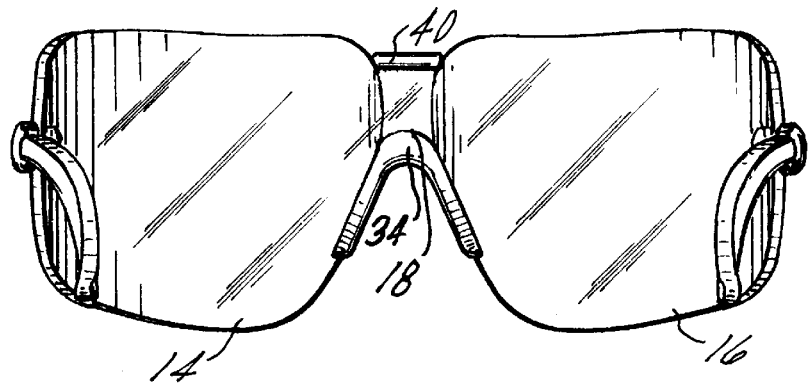
Figure 23:
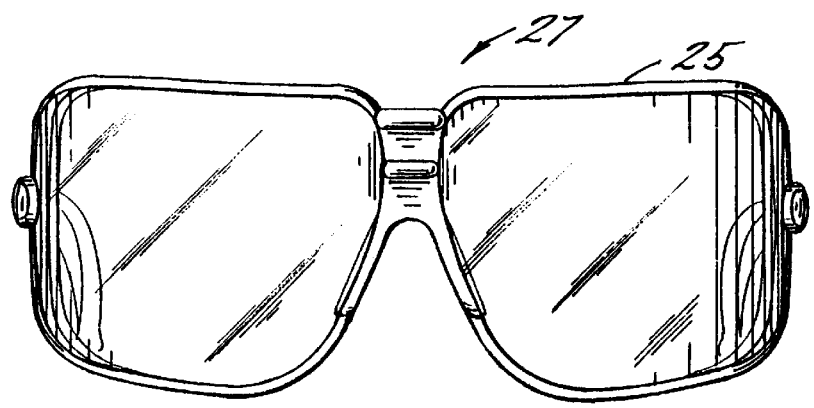
FIGS. 23 and 24 are respective front and side elevation views of a pair of plano eyewear in accordance with the present invention employing a frame surrounding the lens.
Figure 24:
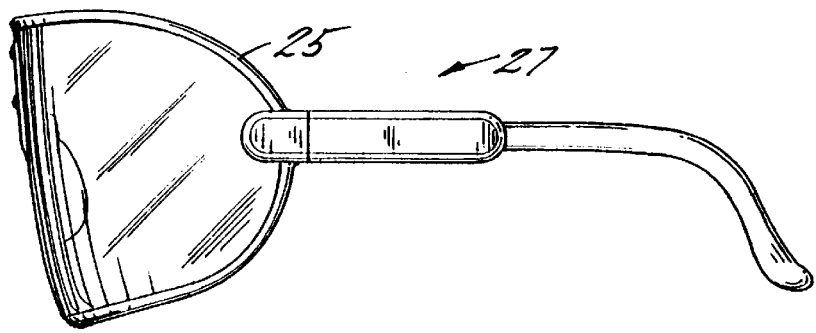

Turning now to FIGS. 19–22, a pair of plano eyewear in accordance with the present invention is shown generally at 20. Eyewear 20 includes a lens 12 of the type shown in FIGS. 13–15. In a preferred embodiment, a pair of temples 22, 24 are hingedly connected directly to the upper, outer edges of each lens 14, 16, respectively. Of course, it will be appreciated that lenses 14, 16 could be connected to a frame and temples 22, 24 in turn may also be connected to such a frame rather than having the temples 22, 24 being connected directly to the lenses 14, 16 as shown in FIG. 19. An example of such an alternative embodiment wherein lens 12 is surrounded by a frame 25 is shown in FIGS. 23 and 24 at 27. Also in a preferred embodiment, a nose piece 26 is snap lockedly attached to connector 18.

Figure 42:
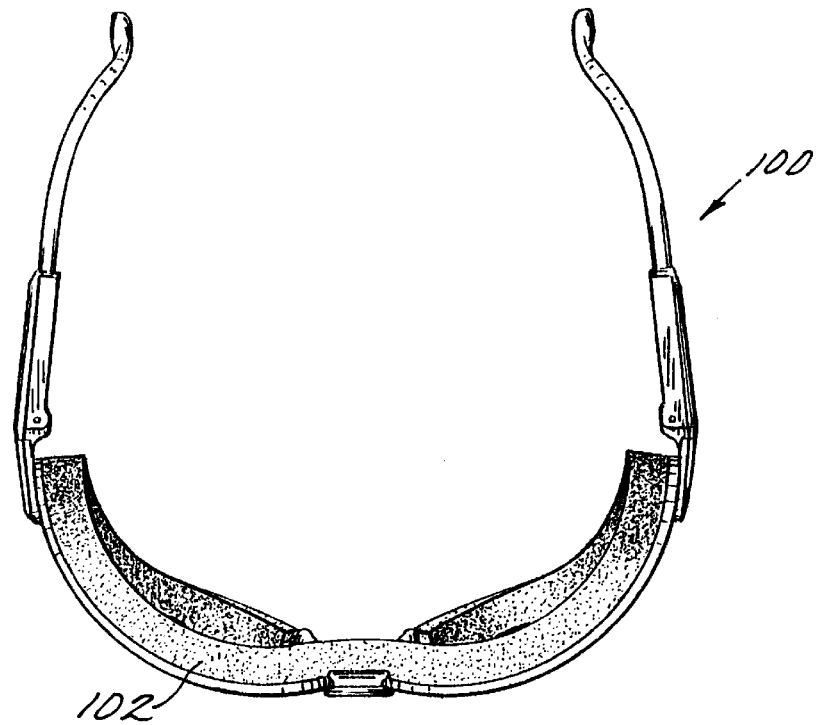
FIGS. 42–44 are respective top plan, front and rear views of eyewear in accordance with this invention which incorporates a resilient foam flange.
Figure 43:
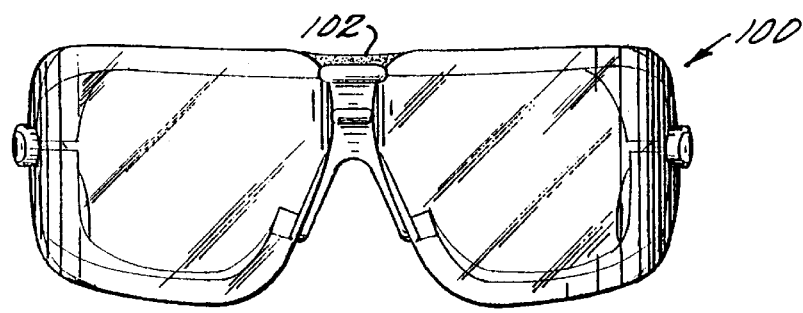
Figure 44:
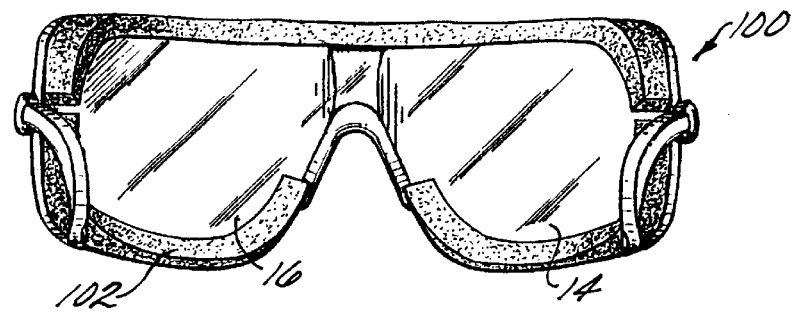

Referring to FIGS. 42–44, an alternative embodiment to the plano eyewear of the present invention is shown generally at 100. Eyewear 100 is identical to the eyewear of FIGS. 19–22 with the exception that eyewear 100 includes a flange 102 comprised of a resilient material, preferably a resilient foam. As best shown in FIGS. 42 and 44, resilient flange 102 may be comprised of one or a plurality of strips which are adhesively applied along the periphery of lenses 14, 16 or may be directly molded onto the lens. The flange may be a single strip in which case it can be run along the entire periphery of the lens including those portions of the nosepiece and the hinge. Preferably, however, as shown in FIG. 44, the flange is broken at the hinges of the temples for ease of closing the temples during storage and the flange is broken at the nosepiece since it may not be required in that area.

The foam flange provides an important feature and advantage to the eyewear of the present invention. In particular, the foam flange 102 tends to minimize the probability of exposure of the wearer's eyes to particulates in a dusty, dirty work environment and/or in a similar dirty or dusty sports environment such as on a beach. Currently, the most common eye injury in the industrial workplace is the result of particulates in the eye. The use of the foam flange 102 will substantially reduce those incidences of eye damage caused by floating particulates for people who wear the eyewear of FIGS. 42–44. Of course, the foam flange depicted in FIGS. 42–44 could also be used in connection with the eyewear of FIGS. 23 and 24 which is associated with a frame 25. Still another feature provided by the resilient flange of the present invention is that the flange, particularly by tailoring the softness and other characteristics of the foam, will improve the wearer's comfort, especially when the eyewear of this invention is worn for long periods of time.

Figure 25A:
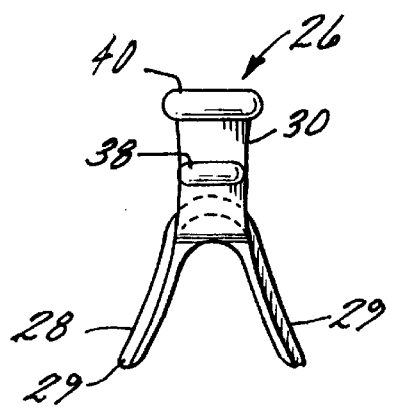
FIGS. 25A and 25B are respective front and side elevation views, depicting a snap-on nose piece in accordance with the present invention.
Figure 25B:
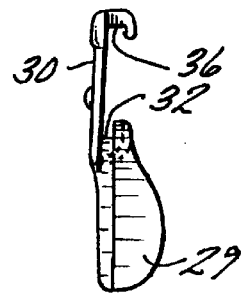

Referring to FIGS. 25A–B, nose piece 26 includes an inverted U or saddle shaped pad area or lower section 28 (consisting of two divergent nose pads 29) which is sized to seat on the bridge of a nose. An upwardly extended clip-on section 30 includes a lower channel 32 which is sized to seat on and be retained by a lower edge 34 of connector 18 and an upper channel 36 defined between section 30 and a resilient detent 30. Channel 36 is similarly sized to seat on and be retained by upper edge 40 of connector 18. Nose piece 26 has a known configuration and is snapped onto connector 18 in a known fashion. A pair of spaced, parallel decorative elongated protrusions with rounded ends 38 and 40 are positioned on the front face of clip-on Section 30. In a preferred embodiment, nose pads 29 extend outwardly and downwardly from the two lenses 14, 16.

Also in a preferred embodiment, lower section 28 (which contacts the wearer's nose) is made from a material having a different or contrasting color, or a different durometer (e.g., softer or stiffer) relative to the material comprising the remaining portion of the nose piece. For example, the material in the nose pad 28 may be comprised of a softer material such as rubber, silicone, soft thermoplastic materials or soft foam materials and the material in the extended clip-on section 30 may be comprised of hard thermoplastic materials (i.e., polycarbonate, ABS, nylon), hard foams or metals.

In accordance with a novel feature of the present invention, the two sections 28 and 30 of differing materials are made in a single co-injection molding step as opposed to prior art processing whereby the two sections 28, 30 would be separately molded and thereafter bonded together. By co-injection molding of the nose piece, substantial savings in both processing time and assembly is achieved. The co-molded sections 28, 30 would remain bonded either through a chemical bond (through proper selection of the two co-molded materials) or through a mechanical bond, or more preferably, through a combination of a chemical and mechanical bond.

Figure 20:
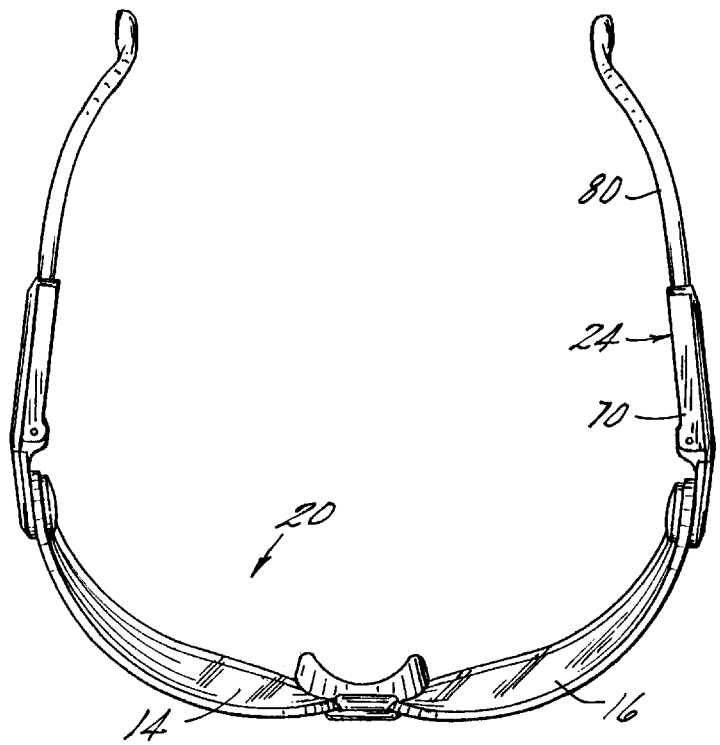
FIGS. 19–22 are respective front, top plan, side elevation and rear views of a pair of plano eyewear in accordance with the present invention.

The temples 22 and 24, shown generally in FIG. 20, include an endpiece 60 and a snap-on retainer 62 which connect the temples 22 and 24 to the outer edge of each lens 14 and 16, respectively. The endpiece 60 is moveably mounted to the outer edge of the lens to allow the user to adjust the pantoscopic angle of the eyewear 20. A temple length adjustment housing 70 is pivotally connected to the endpiece 60 which allows the temples 22 and 24 to be folded towards the lenses 14 and 16. This reduces the size of the eyewear 20 for storage and reduces the likelihood that the temples 22 and 24 will be damaged. A temple tip 80 is movably mounted to the temple length adjustment housing 70 which allows the user to adjust the overall length of the temples 22 and 24. These elements are described in further detail below with reference to FIGS. 26–41.

Figure 26:
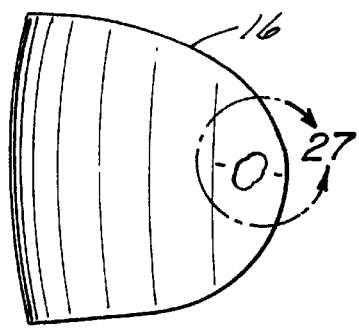
FIG. 26 is a side elevation view of a lens in accordance with this invention depicting the temple attachment and pantoscopic adjustment mechanism.
Figure 28:
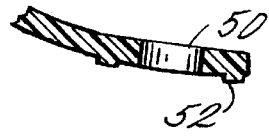
FIG. 28 is a cross-sectional elevation view along the line 28—28 of FIG. 27.

FIG. 26 is a side elevation view of lens 16 shown in FIG. 20. The lens 16 includes a slot 50 and projections 52 which cooperate with the endpiece 60 to provide adjustment of the pantoscopic angle of the eyewear 20. Slot 50 is generally oval shaped and has a center circular area 51. Projections 52 are formed on the surface of the lens 16 and extend away from the lens surface. FIG. 28 is a cross section elevation view along line 28—28 in FIG. 27.

Figure 27:
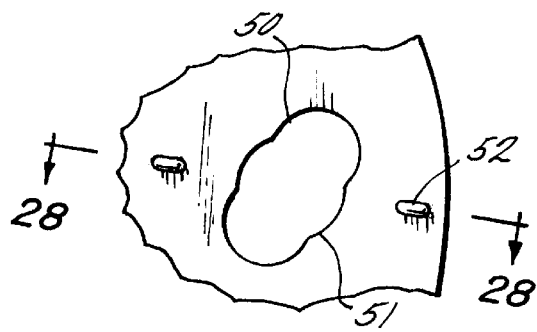
FIG. 27 is an enlarged elevation view of a portion of FIG. 26.
Figure 29:
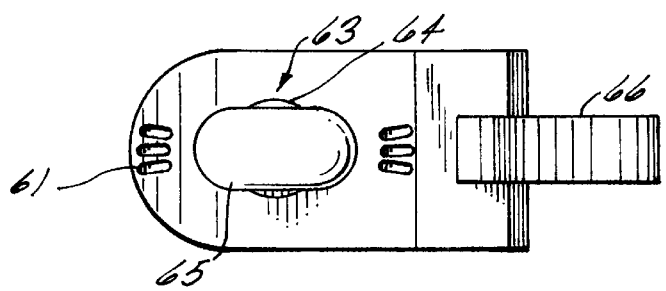
FIG. 29 is a front elevation view of the temple endpiece in accordance with this invention.

FIG. 29 is a front elevation view of the temple endpiece 60. The endpiece 60 has formed therein a plurality of recesses 61 that engage the projections 52 formed on the lens 16. A post, shown generally at 63, has a circular neck 64 and an oblong head 65 which may be oval shaped. An endpiece hinge 66 allows the temple length adjustment housing 70 to be pivotally mounted to the endpiece 60. Although FIGS. 27 and 28 show the projections 52 formed on the lens 16 and the recesses 61 formed on the endpiece 60, it is understood that the location of these elements may be reversed.

Figure 31:
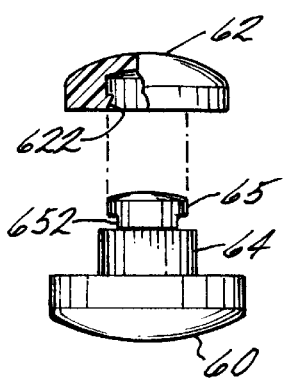
FIGS. 30 and 31 are respective side and end views of the endpiece of FIG. 29 with snap-on retainer.
Figure 30:
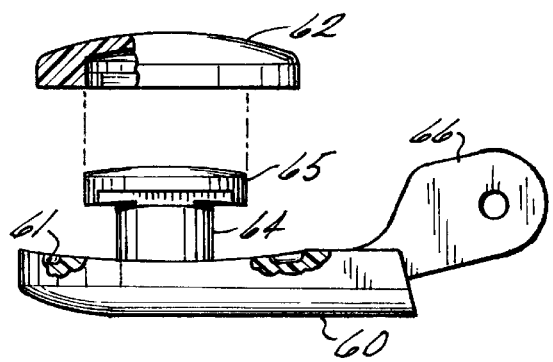
Figure 33:
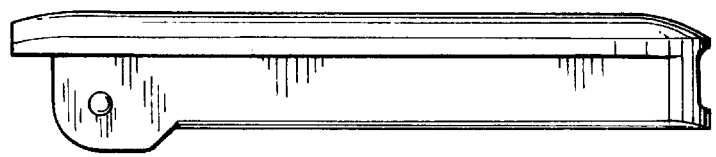
FIGS. 32–35 are respective front, side and end views of the temple length adjustment housing in accordance with this invention.
Figure 34:
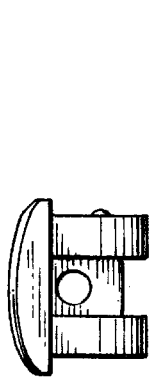
Figure 32:
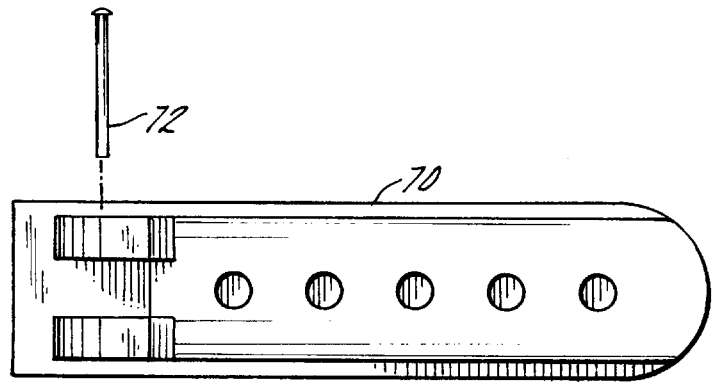
Figure 35:
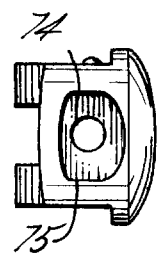
Figure 37:
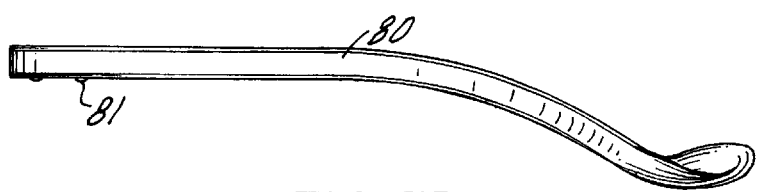
FIGS. 36–37 are respective side and top plan views of the temple tip in accordance with this invention.
Figure 36:
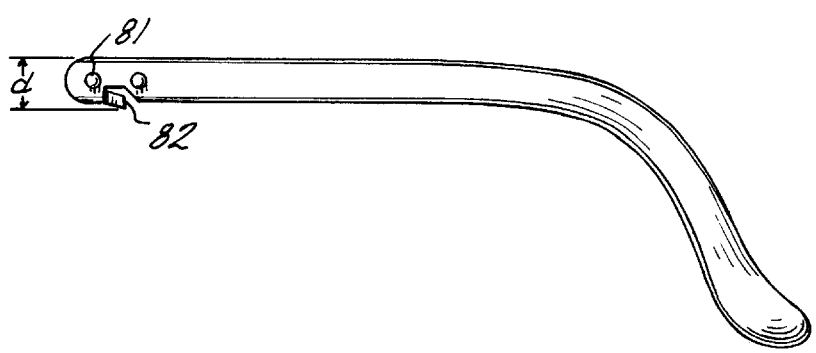

FIGS. 30 and 31 are respective side and end views of the endpiece 60 of FIG. 29 and a snap-on cap 62. The head 65 has an undercut area 652 which engages a projection 622 formed within a cavity in the snap-on cap 62. This prevents the snap-on cap 62 from inadvertently becoming detached from the head 65. The snap-on cap 62 is made from a soft material having a durometer hardness of approximately 90. The method of attaching the endpiece 60 to the lens 16 will now be described.

The head 65 is placed in the slot 50 until the circular neck 64 is adjacent to the circular area 51. The endpiece 60 is then rotated until the recesses 61 are adjacent to the projections 52. The snap-on cap 62 is placed on the head 65 to prevent rough or sharp edges on the head 65 from contacting the wearer's skin. In addition, the outer dimension of the head 65 is greater than the diameter of the circular area 51, which also prevents the endpiece 60 from becoming inadvertently detached from the lens 16. The head 65 must be aligned with the oval slot 50 for the endpiece 60 to be removed from the lens 16. Once the endpiece 60 is mounted to the lens 16, the pantoscopic angle of the eyewear may be easily adjusted. The endpiece 60 is rotated relative to the lens 16 until the projections 52 engage the desired set of recesses 61. In the exemplary embodiment shown in FIG. 29, three sets of recesses 61 are shown, defining three pantoscopic angles. It is understood that more or less recesses 61 may be used to increase or decrease the number of available pantoscopic angles. The interference fit between the projections 52 and the recesses 61 holds the endpiece 60 at the desired pantoscopic angle. The recesses 61 may also be rounded at the top of the recess to eliminate sharp edges and render it easier to change the pantoscopic angle. To alter the pantoscopic angle, the user rotates the endpiece 60 relative to the lens 16 until the desired pantoscopic angle is achieved.

The eyewear of the present invention also allows the user to adjust the length of the temples 22 and 24 shown in FIG. 20. Adjustment of the temple length is described with reference to FIGS. 32–37. FIGS. 32–35 are respective front, side and end views of the temple length adjustment housing 70. The temple length adjustment housing 70 includes a temple hinge 71. The temple hinge 71 is pivotally coupled to the endpiece hinge 66 (shown in FIG. 30) with a pin 72.

The temple length adjustment housing 70 has an interior cavity 74 for receiving the temple tip 80. A series of holes 73 are formed in one side of the cavity 74 for engaging projections 81 formed on the temple tip 80 shown in FIGS. 36 and 37. The temple tip 80 is inserted into the cavity 74 through opening 75. The user slides the temple tip 80 within the cavity 74 until the projections 81 are aligned with the desired holes 73. Although two projections are shown on the temple tip 80, it is understood one projection may be used. The interference fit between the projections 81 and the holes 73 prevents the temple tip 80 from freely sliding within the temple length adjustment housing 70.

Figure 38:
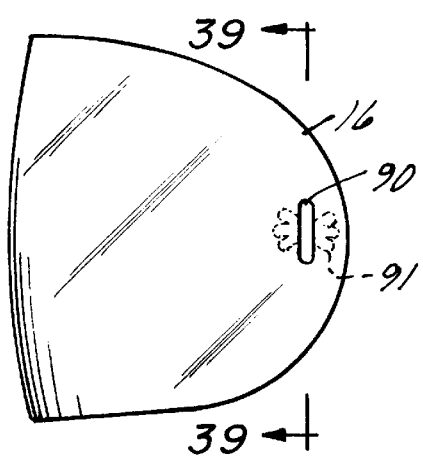
FIG. 38 is a side elevation view of a lens including an alternative temple attachment.
Figure 39:
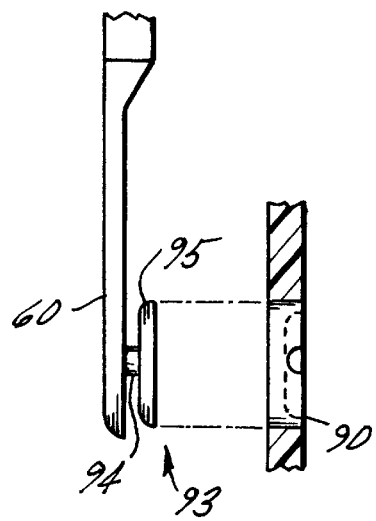
FIG. 39 is a cross-section view along line 39—39 in FIG. 38 and a side elevation view of an endpiece.

A flexible retainer 82 prevents the temple tip 80 from inadvertently becoming removed from the temple length adjustment housing 70. The dimension of the opening 75 to cavity 74 is slightly smaller than the distance, d, from the top of the temple tip 80 and the bottom of the flexible retainer 82. When the temple tip 80 is inserted into the temple length adjustment housing 70, the flexible retainer 82 is forced towards the temple tip 80 so that the temple tip 80 can enter the cavity 74. Once the flexible retainer 82 has completely passed the opening 75, the flexible retainer 82 returns to its original position. The flexible retainer 82 will contact the inside of the opening 75 and prevent the temple tip 80 from being inadvertently removed from the temple length adjustment housing 70. A slot (not shown in the drawings) is provided on the bottom of the temple length adjustment housing 70 so that the flexible retainer 82 can be pressed towards the temple tip 80 in order to remove the temple tip 80 from the temple length adjustment housing 70. FIGS. 38–41 illustrate an alternative pantoscopic angle adjustment arrangement. FIG. 38 is a side elevation view of lens 16 which has slot 90 formed through the lens 16. On the back surface of the lens 16 are a series of recesses 91 which define various pantoscopic angles. FIG. 39 is a cross sectional view taken along line 39—39 in FIG. 38 and a side elevation view of an endpiece 60. As shown in FIG. 39, the endpiece 60 has a post, shown generally at 93, having a head 95 and a neck 94. The head is shaped so as to fit through slot 90 and to fit within recesses 91.

Figure 41:
FIG. 41 is a cross section view along line 41—41 in FIG. 40.
Figure 40:
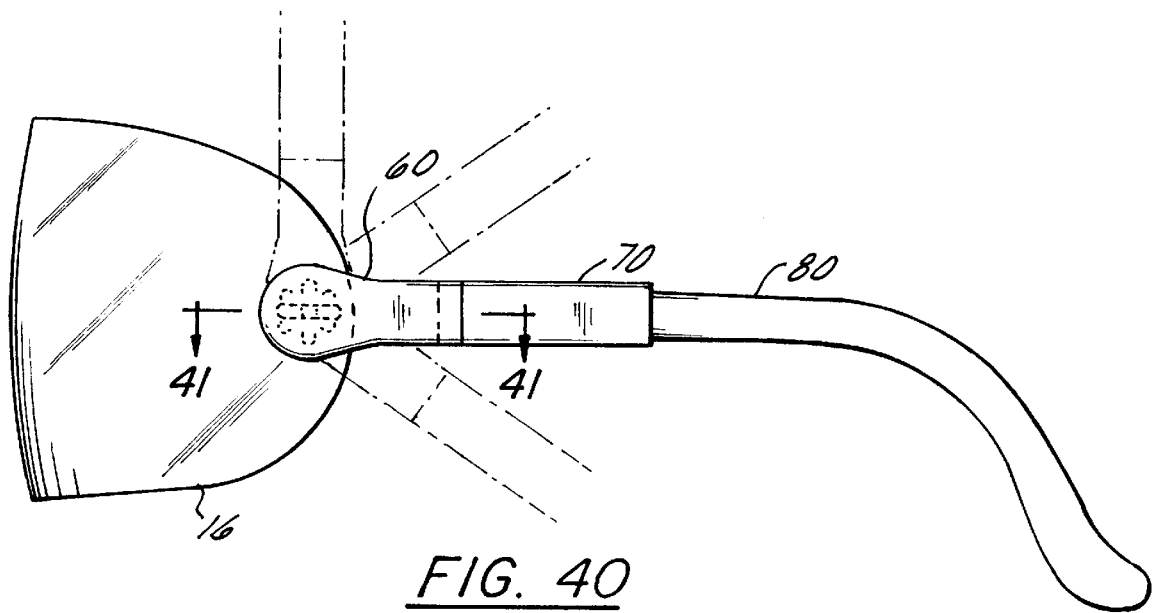
FIG. 40 is a side elevation view of a temple attached to the lens shown in FIG. 38.

The endpiece 60 is attached to the lens 16 by first aligning the head 95 with the slot 90 and placing the head 95 within the slot 90. The endpiece 60 is then rotated over the lens thickness until the head 95 engages the recess 91 that provides the desired pantoscopic angle. The pantoscopic angle may be adjusted by rotating the endpiece 60 until the head 95 engages the next recess 91. To aid in adjusting the pantoscopic angle, the tops of the recesses 91 may be slightly rounded to eliminate sharp edges and make the transition from one recess to the next easier. The interference fit between the head 95 and the recess 91 holds the endpiece 60 in place. FIG. 40 shows the endpiece 60 attached to the lens 16 along with the temple length adjustment housing 70 and temple tip 80. FIG. 41 is a cross section view along line 41—41 in FIG. 40. The head 95 is preferably made from a resilient plastic so that the head can flex when being rotated from one recess to the next and snap firmly into a recess once aligned.

While preferred embodiments have been shown and described, various modifications and substitutions may be made thereto without departing from the spirit and scope of the invention. Accordingly, it is to be understood that the present invention has been described by way of illustrations and not limitation.

What is claimed is:

1. Eyewear comprising:
    a lens having a first surface and a second surface spaced from the first surface, said lens further having a viewing portion;
    said first surface comprising a section of a 3-dimensional surface defined by rotating an ellipse about an axis, which axis is not an axis of said ellipse, and which is offset from the major or minor axis of the ellipse;
    said second surface having a curvature which, together with said first surface, provides piano optics to at least said viewing portion; and
    a support structure for positioning said lens at a location spaced from the eyes of the wearer.
2. The eyewear of claim 1 including:
    a resilient flange along at least a portion of the periphery of said lens.
3. The eyewear of claim 2 wherein:
    said resilient flange comprises a foam flange.
4. The eyewear of claim 1 wherein said eyewear comprises spectacles.
5. The eyewear of claim 1 wherein:
    said lens comprises dual lens sections, one lens section being associated with each eye of a wearer.
6. The eyewear of claim 5 wherein:
    said dual lens sections are interconnected by an integral bar.
7. The eyewear of claim 1 wherein:
    said lens comprises a continuous lens for wrapping about both temples of a wearer.
8. The eyewear of claim 1 wherein:
    said plano optics is further provided by varying the thickness between said spaced first and second surfaces of said lens.
9. The eyewear of claim 1 wherein:
    the entirety of said lens has plano optics.
10. The eyewear of claim 1 wherein:
    said lens is comprised of molded plastic material.
11. The eyewear of claim 1 wherein:
    said ellipse has a major axis of 4.125 centimeters in length and a minor axis of 4.0 centimeters in length.
12. The eyewear of claim 4 wherein:
    said spectacles include a pair of temples.
13. The eyewear of claim 4 wherein:
    said spectacles include a nose bridge.
14. The eyewear of claim 12 wherein:
    said spectacles include a nose bridge.
15. The eyewear of claim 1 including:
    a frame at least partially surrounding said lens.
16. The eyewear of claim 15 wherein:
    said frame fully surrounds said lens.
17. The eyewear of claim 1 wherein:
    said eyewear is selected from the group consisting of visors, goggles, masks and helmets.
18. The eyewear of claim 1 wherein:
    said lens comprises formed polymeric material.
19. The eyewear of claim 16 wherein:
    said temples are hingedly attached to said lens.
20. Eyewear comprising:
    a lens having a first surface and a second surface spaced from the first surface, said lens further having a viewing portion;
    said first surface comprising a section of a 3-dimensional surface defined by rotating an aspheric shape about an axis, which axis is not an axis of said aspheric shape, and which is offset from an axis of said aspheric shape;
    said second surface having a curvature which, together with said first surface, provides plano optics to at least said viewing portion; and a support structure for positioning said lens at a location spaced from the eyes of the wearer.

21. The eyewear of claim 20 wherein said eyewear comprises spectacles.

22. The eyewear of claim 21 wherein:

said spectacles include a pair of temples.

23. The eyewear of claim 22 wherein:

said temples are hingedly attached to said lens.

24. The eyewear of claim 20 wherein:

said lens comprises dual lens sections, one lens section being associated with each eye of a wearer.

25. The eyewear of claim 24 wherein:

said dual lens sections are interconnected by an integral bar.

26. The eyewear of claim 20 wherein:

said lens comprises a continuous lens for wrapping about both temples of a wearer.

27. The eyewear of claim 20 wherein:

the entirety of said lens has piano optics.

28. The eyewear of claim 20 wherein:

said lens is comprised of molded plastic material.

29. The eyewear of claim 21 wherein:

said spectacles include a nosepiece.

30. The eyewear of claim 22 wherein:

said spectacles include a nosepiece.

31. The eyewear of claim 20 including:

a frame at least partially surrounding said lens.

32. The eyewear of claim 31 wherein:

said frame fully surrounds said lens.

33. The eyewear of claim 20 wherein:

said lens comprises formed polymeric material.

34. The eyewear of claim 20 wherein:

said eyewear is selected from the group consisting of visors, goggles, masks and helmets.

35. A lens comprising:

a first surface and a second surface spaced from said first surface, said lens further having a viewing portion;

said first surface comprising a section of a 3-dimensional surface which is defined by rotating an aspheric shape about an axis, which axis is not an axis of said aspheric shape, and which is offset from an axis of said aspheric shape;

said second surface having a curvature which, together with said first surface, provides piano optics to at least said viewing portion of said lens; and said lens comprising a dual lens section interconnected by a bar.

36. A lens comprising:

a first surface and a second surface spaced from said first surface, said lens further having a viewing portion;

said first surface comprising a section of a 3-dimensional surface which is defined by rotating an aspheric shape about an axis, which axis is not an axis of said aspheric shape, and which is offset from an axis of said aspheric shape;

said second surface having a curvature which, together with said first surface, provides piano optics to at least said viewing portion of said lens; and a resilient flange along at least a portion of the periphery of said lens.

37. The lens of claim 36 wherein:

said resilient flange comprises a foam flange.

38. Eyewear comprising:

a lens having a first surface and a second surface spaced from the first surface, said lens further having a viewing portion;

said first surface comprising a section of a 3-dimensional surface defined by rotating an ellipse about an axis, which axis is not an axis of said ellipse, and which is offset from the major or minor axis of the ellipse;

said second surface having a curvature which, together with said first surface, provides plano optics to at least said viewing portion; and a resilient flange along at least a portion of the periphery of said lens.

39. The eyewear of claim 38 wherein:

said resilient flange comprises a foam flange.

40. Eyewear comprising:

a lens having a first surface and a second surface spaced from the first surface, said lens further having a viewing portion;

said first surface comprising a section of a 3-dimensional surface defined by rotating an ellipse about an axis, which axis is not an axis of said ellipse, and which is offset from the major or minor axis of the ellipse;

said second surface having a curvature which, together with said first surface, provides piano optics to at least said viewing portion; and wherein said eyewear comprises spectacles.

41. The eyewear of claim 40 wherein said spectacles include:

a pair of temples.

42. The eyewear of claim 41 wherein:

said temples are hingedly attached to said lens.

43. The eyewear of claim 40 wherein:

said spectacles include a nosepiece.

44. The eyewear of claim 41 wherein:

said spectacles include a nosepiece.

45. The eyewear of claim 40 wherein:

said lens comprises dual lens sections, one lens section being associated with each eye of the wearer.

46. The eyewear of claim 45 wherein:

said dual lens sections are interconnected by an integral bar.

47. The eyewear of claim 40 wherein:

said lens comprises a continuous lens for wrapping about both temples of a wearer.

48. The eyewear of claim 40 wherein:

said lens comprises formed polymeric material.

49. A lens comprising:

a first surface and a second surface spaced from said first surface, said lens further having a viewing portion;

said first surface comprising a section of a 3-dimensional surface which is defined by rotating an ellipse about an axis which is coplanar, parallel to, and offset from an axis of said ellipse;

said second surface having a curvature which, together with said first surface, provides piano optics to at least said viewing portion of said lens; and a resilient flange along at least a portion of the periphery of said lens.

50. The lens of claim 49 wherein:

said resilient flange comprises a foam flange.

51. Eyewear comprising:

a lens having a first surface and a second surface spaced from the first surface, said lens further having a viewing portion;

said first surface comprising a section of a 3-dimensional surface defined by rotating an aspheric shape about an axis, which is not an axis of said aspheric shape, and which is offset from an axis of said aspheric shape;

said second surface having a curvature which, together with said first surface, provides piano optics to at least said viewing portion; and wherein said eyewear comprises spectacles.

52. The eyewear of claim 51 wherein said spectacles include:

a pair of temples.

53. The eyewear of claim 52 wherein:

said temples are hingedly attached to said lens.

54. The eyewear of claim 51 wherein:

said lens is comprised of formed polymeric material.

55. The eyewear of claim 51 wherein:

said lens comprises dual lens sections, one lens section being associated with each eye of a wearer.

56. The eyewear of claim 55 wherein:

said dual lens sections are interconnected by an integral bar.

57. Eyewear comprising:

a lens having a first surface and a second surface spaced from the first surface, sand lens further having a viewing portion;

said first surface comprising a section of a 3-dimensional surface defined by rotating an aspheric shape about an axis, which axis is not an axis of said aspheric shape, and which is offset from an axis of said aspheric shape;

said second surface having a curvature which, together with said first surface, provides piano optics to at least said viewing portion; and wherein said lens comprises a continuous lens for wrapping about both temples of a wearer.

58. A lens comprising:

a first surface and a second surface spaced from said first surface, said lens further having a viewing portion;

said first surface comprising a section of a 3-dimensional surface which is defined by rotating an aspheric shape about an axis which is offset from an axis of said aspheric shape; and said second surface having a curvature which, together with said first surface, provides piano optics to at least said viewing portion of said lens; and wherein said aspheric shape comprises an ellipse, said ellipse having a major axis of 4.125 centimeters in length and a minor axis of 4.0 centimeters in length.

59. Eyewear comprising:

a lens having a first surface and a second surface spaced from the first surface, said lens further having a viewing portion;

said first surface comprising a section of a 3-dimensional surface defined by rotating an ellipse about an axis which is offset from the major or minor axis of the ellipse;

said second surface having a curvature which, together with said first surface, provides piano optics to at least said viewing portion; and said ellipse having a major axis of 4.125 centimeters in length and a minor axis of 4.0 centimeters in length.

60. A lens comprising:

a first surface and a second surface spaced from the first surface, the distance between said first and second surfaces defining the tens thickness, said lens further having a viewing portion;

said first surface having a cross-section in a first axis which is a segment of an ellipse and a cross-section in a second axis which is a segment of a circle;

said second surface having a curvature which varies the thickness of the lens to provide piano optics to at least said viewing portion; and said ellipse having a major axis of 4.125 centimeters in length and a minor axis of 4.0 centimeters in length.

61. In eyewear which includes a piano lens, said plano lens having a first surface and a second surface, the distance between said first and second surfaces defining the lens thickness, said plano lens further having a viewing portion, the improvement comprising:

said first surface having a cross-section in a first axis which is a segment of an ellipse and a cross-section in a second axis which is a segment of a circle;

said second surface having a curvature which varies the thickness of the lens to provide piano optics to at least said viewing portion; and said ellipse having a major axis of 4.125 centimeters in length and a minor axis of 4.0 centimeters in length.

62. A lens comprising:

a first surface and a second surface spaced from said first surface, said lens further having a viewing portion;

said first surface comprising a section of a 3-dimensional surface which is defined by rotating an ellipse about an axis which is coplanar, parallel to, and offset from, an axis of said ellipse;

said second surface having a curvature which together with first surface, provides plano optics to at least said viewing portion of said lens; and said ellipse having a major axis of 4.125 centimeters in length and a minor axis of 4.0 centimeters in length.

* * * * *

UNITED STATES PATENT AND TRADEMARK OFFICE
CERTIFICATE OF CORRECTION

PATENT NO. : 5,825,455
DATED : October 20, 1998
INVENTOR(S) : Keith Fecteau, et al.

It is certified that error appears in the above-identified patent and that said Letters Patent is hereby corrected as shown below:

Column 3,
Line 19, delete "non-discemable" and insert therefor -- non-discernible --

Column 4,
Line 5, delete "piano" and insert therefor -- plano --

Column 9,
Line 29, delete "30" and insert therefor -- 38 --

Column 12,
Line 6, delete "piano" and insert therefor -- plano --

Column 13,
Line 20, delete "piano" and insert therefor -- plano --
Line 47, delete "piano" and insert therefor -- plano --
Line 61, delete "piano" and insert therefor -- plano --

Column 14,
Line 25, delete "piano" and insert therefor -- plano --
Line 58, delete "piano" and insert therefor -- plano --

Column 15,
Line 6, delete "piano" and insert therefor -- plano --
Line 33, delete "piano" and insert therefor -- plano --
Line 46, delete "piano" and insert therefor -- plano --

Column 16,
Line 6, delete "piano" and insert therefor -- plano --
Line 14, delete "tens" and insert therefor -- lens --
Line 21, delete "piano" and insert therefor -- plano --

UNITED STATES PATENT AND TRADEMARK OFFICE
CERTIFICATE OF CORRECTION

PATENT NO. : 5,825,455
DATED : October 20, 1998
INVENTOR(S) : Keith Fecteau, et al.

It is certified that error appears in the above-identified patent and that said Letters Patent is hereby corrected as shown below:

<u>Column 16 contd.</u>
Line 25, delete "piano" and insert therefor -- plano --
Line 49, insert -- said -- between "with" and "first"

Signed and Sealed this

Twenty-fifth Day of September, 2001

Attest:

NICHOLAS P. GODICI
Attesting Officer     *Acting Director of the United States Patent and Trademark Office*

(12) EX PARTE REEXAMINATION CERTIFICATE (5529th)
United States Patent
Fecteau et al.

(10) Number: US 5,825,455 C1
(45) Certificate Issued: Sep. 26, 2006

(54) ASPHERIC PLANO EYEWEAR

(75) Inventors: Keith Fecteau, Wilbraham, MA (US); James Hall, Lincoln, RI (US); Raoul Desy, Sturbridge, MA (US); John Salce, Auburn, MA (US); David M. Hasenauer, Monrovia, CA (US)

(73) Assignee: Cabot Safety Intermediate Corporation, Southbridge, MA (US)

Reexamination Request:
No. 90/006,862, Nov. 14, 2003

Reexamination Certificate for:
Patent No.: 5,825,455
Issued: Oct. 20, 1998
Appl. No.: 08/806,832
Filed: Feb. 26, 1997

Certificate of Correction issued Sep. 25, 2001.

Related U.S. Application Data

(63) Continuation-in-part of application No. 08/641,901, filed on May 2, 1996, now abandoned.

(51) Int. Cl.
*G02C 7/02* (2006.01)
*G02C 1/13* (2006.01)

(52) U.S. Cl. ........................................ 351/159; 351/41
(58) Field of Classification Search ................ 351/159, 351/160 R, 160 H, 41, 43–44; 2/6.3, 425, 2/426
See application file for complete search history.

(56) References Cited

U.S. PATENT DOCUMENTS

| 1,741,536 A | 12/1929 | Rayton ........................ 351/159 |
| 1,942,400 A | 1/1934 | Glancy ........................ 351/172 |
| 3,218,765 A | 11/1965 | Volk ............................ 451/42 |
| 3,722,986 A | 3/1973 | Tagnon ........................ 351/176 |
| 4,613,217 A | 9/1986 | Fuerter et al. ............... 351/159 |
| 4,859,048 A | 8/1989 | Jannard ....................... 351/159 |
| 4,934,807 A | 6/1990 | Bolle et al. .................... 351/62 |
| 5,204,700 A | 4/1993 | Sansalone .................... 351/43 |
| 5,319,007 A | 6/1994 | Bright ......................... 351/159 |
| 5,347,323 A | 9/1994 | Wilson ......................... 351/44 |
| 5,604,547 A | 2/1997 | Davis et al. .................. 351/44 |
| 5,648,832 A | 7/1997 | Houston et al. ............. 351/159 |
| 5,757,457 A | 5/1998 | Conway ..................... 351/138 |
| 5,774,201 A | 6/1998 | Tackles ....................... 351/159 |

OTHER PUBLICATIONS

*Cabot Safety Intermediate Corporation and Aearo Company v. Crews, Inc.*; Civil Action No. 02–CV–30182(NMG).
Fannin, Troy, "Clinical Optics", 1987, pp. 28, 29, 31, 32, 173, 174 & 369.
Morgan, Meredith, "The Optics of Ophthalmic Lenses", 1978, pp. 21–24.
Funk & Wagnalls, "New Comprehensive International Dictionary of the English Language, Encyclopedic Edition", 1977, p. 1326.

*Primary Examiner*—Scott J. Sugarman

(57) ABSTRACT

A novel plano lens and eyewear incorporating such lens is presented wherein the plano lens comprises a front surface curvature which is created by rotating an aspheric shape about an axis which is offset from an axis of the aspheric shape. In a preferred embodiment, the aspheric shape is an ellipse or at least is an aspheric shape, a segment of which has an elliptical arc. This elliptical arc is rotated about an axis spaced (offset) some distance from a major or minor axis of the ellipse. In a more preferred embodiment, the ellipse is rotated about an axis spaced from and parallel to the major or minor axis of the ellipse, but in the same plane as the ellipse. The resulting surface of this preferred lens configuration will have a cross-section in a first axis which is a segment of an ellipse, and a cross-section in a second axis (perpendicular to the first axis) which is a segment of a circle. A significant feature of the preferred front lens configuration is that the surface generated is rotationally symmetric.

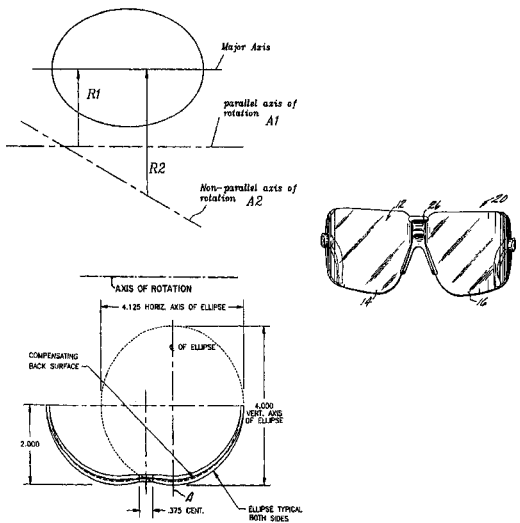

EX PARTE REEXAMINATION CERTIFICATE ISSUED UNDER 35 U.S.C. 307

THE PATENT IS HEREBY AMENDED AS INDICATED BELOW.

Matter enclosed in heavy brackets [ ] appeared in the patent, but has been deleted and is no longer a part of the patent; matter printed in italics indicates additions made to the patent.

AS A RESULT OF REEXAMINATION, IT HAS BEEN DETERMINED THAT:

The patentability of claims 1–62 is confirmed.

New claims 63–94 are added and determined to be patentable.

63. *Eyewear comprising:*
*a lens having a first surface and a second surface spaced from the first surface, said lens further having a viewing portion;*
*said first surface comprising a section of a 3-dimensional surface defined by rotating an ellipse about an axis, which axis is not an axis of said ellipse, and which is offset from the major or minor axis of the ellipse;*
*said second surface having a curvature which, together with said first surface, provides plano optics to at least said viewing portion;*
*wherein said lens has horizontal and vertical cross-sections, the vertical cross-section having a curvature which is other than a straight line; and*
*a support structure for positioning said lens at a location spaced from the eyes of the wearer.*

64. *The eyewear of claim 63 including:*
*a resilient flange along at least a portion of the periphery of said lens.*

65. *The eyewear of claim 63 wherein said eyewear comprises spectacles.*

66. *The eyewear of claim 63 wherein:*
*said lens comprises dual lens sections, one lens section being associated with each eye of a wearer.*

67. *The eyewear of claim 63 wherein:*
*said lens comprises a continuous lens for wrapping about both temples of a wearer.*

68. *The eyewear of claim 63 wherein:*
*said plano optics is further provided by varying the thickness between said spaced first and second surfaces of said lens.*

69. *The eyewear of claim 63 wherein:*
*the entirety of said lens has plano optics.*

70. *The eyewear of claim 63 wherein:*
*said lens is comprised of molded plastic material.*

71. *The eyewear of claim 63 wherein:*
*said eyewear is selected from the group consisting of visors, goggles, masks and helmets.*

72. *Eyewear comprising:*
*a lens having a first surface and a second surface spaced from the first surface, said lens further having a viewing portion;*
*said first surface comprising a section of a 3-dimensional surface defined by rotating an aspheric shape about an axis, which axis is not an axis of said aspheric shape, and which is offset from an axis of said aspheric shape;*
*said second surface having a curvature which, together with said first surface, provides plano optics to at least said viewing portion;*
*wherein said lens has horizontal and vertical cross-sections, the vertical cross-section having a curvature which is other than a straight line; and*
*a support structure for positioning said lens at a location spaced from the eyes of the wearer.*

73. *The eyewear of claim 72 wherein said eyewear comprises spectacles.*

74. *The eyewear of claim 72 wherein:*
*said lens comprises dual lens sections, one lens section being associated with each eye of a wearer.*

75. *The eyewear of claim 72 wherein:*
*said lens comprises a continuous lens for wrapping about both temples of a wearer.*

76. *The eyewear of claim 72 wherein:*
*the entirety of said lens has plano optics.*

77. *The eyewear of claim 72 wherein:*
*said lens is comprised of molded plastic material.*

78. *The eyewear of claim 72 wherein:*
*said eyewear is selected from the group consisting of visors, goggles, masks and helmets.*

79. *Eyewear comprising:*
*a lens having a first surface and a second surface spaced from the first surface, said lens further having a viewing portion;*
*said first surface comprising a section of a 3-dimensional surface defined by rotating an ellipse about an axis, which axis is not an axis of said ellipse, and which is offset from the major or minor axis of the ellipse with the distance of such offset being less than an infinite distance from the major or minor axis of the ellipse;*
*said second surface having a curvature which, together with said first surface, provides plano optics to at least said viewing portion; and*
*a support structure for positioning said lens at a location spaced from the eyes of the wearer.*

80. *The eyewear of claim 79 including:*
*a resilient flange along at least a portion of the periphery of said lens.*

81. *The eyewear of claim 79 wherein said eyewear comprises spectacles.*

82. *The eyewear of claim 79 wherein:*
*said lens comprises dual lens sections, one lens section being associated with each eye of a wearer.*

83. *The eyewear of claim 79 wherein:*
*said lens comprises a continuous lens for wrapping about both temples of a wearer.*

84. *The eyewear of claim 79 wherein:*
*said plano optics is further provided by varying the thickness between said spaced first and second surfaces of said lens.*

85. *The eyewear of claim 79 wherein:*
*the entirety of said lens has plano optics.*

86. *The eyewear of claim 79 wherein:*
*said lens is comprised of molded plastic material.*

87. *The eyewear of claim 79 wherein:*
*said eyewear is selected from the group consisting of visors, goggles, masks and helmets.*

88. *Eyewear comprising:*
*a lens having a first surface and a second surface spaced from the first surface, said lens further having a viewing portion;* said first surface comprising a section of a 3-dimensional surface defined by rotating an aspheric shape about an axis, which axis is not an axis of said aspheric shape, and which is offset from an axis of said aspheric shape with the distance of such offset being less than an infinite distance from any axis of said aspheric shape;

said second surface having a curvature which, together with said first surface, provides plano optics to at least said viewing portion; and a support structure for positioning said lens at a location spaced from the eyes of the wearer.

89. The eyewear of claim 88 wherein said eyewear comprises spectacles.

90. The eyewear of claim 88 wherein:
said lens comprises dual lens sections, one lens section being associated with each eye of a wearer.
91. The eyewear of claim 88 wherein:
said lens comprises a continuous lens for wrapping about both temples of a wearer.
92. The eyewear of claim 88 wherein:
the entirety of said lens has plano optics.
93. The eyewear of claim 88 wherein:
said lens is comprised of molded plastic material.
94. The eyewear of claim 88 wherein:
said eyewear is selected from the group consisting of visors, goggles, masks and helmets.

* * * * *